US009719018B2

United States Patent
Mizusaki et al.

(10) Patent No.: US 9,719,018 B2
(45) Date of Patent: Aug. 1, 2017

(54) MONOMER, LIQUID CRYSTAL COMPOSITION, LIQUID CRYSTAL DISPLAY DEVICE, AND PRODUCTION METHOD FOR LIQUID CRYSTAL DISPLAY DEVICE

(71) Applicants: Sharp Kabushiki Kaisha, Osaka-shi, Osaka (JP); Toyo Gosei Co., Ltd., Ichikawa-shi, Chiba (JP)

(72) Inventors: Masanobu Mizusaki, Osaka (JP); Youhei Nakanishi, Osaka (JP); Takeshi Noma, Osaka (JP); Satoshi Enomoto, Inzai (JP)

(73) Assignees: Sharp Kabushiki Kaisha, Sakai (JP); Toyo Gosei Co., Ltd., Chiba (JP)

( * ) Notice: Subject to any disclaimer, the term of this patent is extended or adjusted under 35 U.S.C. 154(b) by 0 days.

(21) Appl. No.: 14/436,514

(22) PCT Filed: Oct. 17, 2013

(86) PCT No.: PCT/JP2013/078238
§ 371 (c)(1),
(2) Date: Apr. 17, 2015

(87) PCT Pub. No.: WO2014/061757
PCT Pub. Date: Apr. 24, 2014

(65) Prior Publication Data
US 2015/0247090 A1 Sep. 3, 2015

(30) Foreign Application Priority Data
Oct. 19, 2012 (JP) ................................. 2012-232328

(51) Int. Cl.
*C09K 19/56* (2006.01)
*C09K 19/12* (2006.01)
(Continued)

(52) U.S. Cl.
CPC .............. *C09K 19/56* (2013.01); *C07C 69/54* (2013.01); *C07J 9/00* (2013.01); *C07J 17/00* (2013.01);
(Continued)

(58) Field of Classification Search
CPC .... C09K 19/20; C09K 19/36; C09K 19/2028; C09K 19/52; C09K 19/56;
(Continued)

(56) References Cited

U.S. PATENT DOCUMENTS 6,746,729 B1 6/2004 Cherkaoui et al.
2003/0231272 A1 12/2003 Nakamura et al.
(Continued)

FOREIGN PATENT DOCUMENTS

CN 1347401 A 5/2002
CN 1556787 A 12/2004
(Continued)

OTHER PUBLICATIONS

Masuoka et al, "The inhibition of Uric Acid Formation Catalyzed by Xanthine Oxidase Properties of Alkyl Caffeates and Cardol", Journal of Food Research; vol. 1, No. 3; pp. 257-262, 2012.*
(Continued)

*Primary Examiner* — Cynthia H Kelly
*Assistant Examiner* — Anna Malloy
(74) *Attorney, Agent, or Firm* — Keating & Bennett, LLP

(57) ABSTRACT

The present invention provides a liquid crystal composition for forming a polymer layer capable of keeping high voltage holding ratio. The liquid crystal composition in an aspect of the present invention contains a liquid crystal material and one or more kind monomers and, at least one of the monomers is a compound produced by further bonding a hydrocarbon group with 12 carbon atoms or more to a compound produced by bonding two polymerizable groups (Continued)

to a cyclic aliphatic compound or aromatic compound with 6 carbon atoms or more.

15 Claims, 3 Drawing Sheets

(51) Int. Cl.
| | | |
|---|---|---|
| *C09K 19/20* | (2006.01) | |
| *C09K 19/36* | (2006.01) | |
| *C07C 69/54* | (2006.01) | |
| *G02F 1/1337* | (2006.01) | |
| *G02F 1/1341* | (2006.01) | |
| *C09K 19/06* | (2006.01) | |
| *C09K 19/52* | (2006.01) | |
| *C07J 9/00* | (2006.01) | |
| *C07J 17/00* | (2006.01) | |
| *C09K 19/04* | (2006.01) | |
| *C09K 3/10* | (2006.01) | |

(52) U.S. Cl.
CPC ............ *C09K 19/062* (2013.01); *C09K 19/20* (2013.01); *C09K 19/2028* (2013.01); *C09K 19/36* (2013.01); *C09K 19/52* (2013.01); *G02F 1/1341* (2013.01); *G02F 1/133711* (2013.01); *G02F 1/133788* (2013.01); *C09K 3/10* (2013.01); *C09K 2019/0448* (2013.01); *C09K 2019/122* (2013.01); *G02F 2001/133715* (2013.01)

(58) Field of Classification Search
CPC ...... C09K 2019/0448; C09K 2019/122; C09K 19/062; C09K 19/122; G02F 1/133711; G02F 1/133788; G02F 2001/133715; C07C 69/54
See application file for complete search history.

(56) References Cited

U.S. PATENT DOCUMENTS

| | | |
|---|---|---|
| 2005/0040364 A1 | 2/2005 | Cherkaoui et al. |
| 2007/0206129 A1 | 9/2007 | Nakamura et al. |
| 2007/0257230 A1 | 11/2007 | Cherkaoui et al. |
| 2009/0103011 A1 | 4/2009 | Bernatz et al. |
| 2009/0324853 A1 | 12/2009 | Bernatz et al. |
| 2010/0304148 A1 | 12/2010 | Hirai et al. |
| 2011/0261278 A1 | 10/2011 | Oh et al. |
| 2013/0048912 A1 | 2/2013 | Ito |
| 2013/0169916 A1 | 7/2013 | Mizusaki et al. |
| 2014/0168586 A1 | 6/2014 | Mizusaki et al. |

FOREIGN PATENT DOCUMENTS

| | | |
|---|---|---|
| CN | 1890348 A | 1/2007 |
| CN | 101418220 A | 4/2009 |
| JP | 2004-184846 A | 7/2004 |
| JP | 2010-107536 A | 5/2010 |
| JP | 2010-241791 A | 10/2010 |
| JP | 2011-227453 A | 11/2011 |
| WO | 2011/142299 A1 | 11/2011 |
| WO | 2012/032857 A1 | 3/2012 |
| WO | 2012/121319 A1 | 9/2012 |

OTHER PUBLICATIONS

CAPLUS 2006: 1310988.*
Official Communication issued in International Patent Application No. PCT/JP2013/078238, mailed on Jan. 21, 2014.

* cited by examiner

MONOMER, LIQUID CRYSTAL COMPOSITION, LIQUID CRYSTAL DISPLAY DEVICE, AND PRODUCTION METHOD FOR LIQUID CRYSTAL DISPLAY DEVICE

TECHNICAL FIELD

An aspect of the present invention relates to a liquid crystal composition, a liquid crystal display device, a production method for a liquid crystal display device and so on. More particularly, an aspect of the present invention relates to a liquid crystal composition for forming a polymer layer by which alignment of liquid crystal molecules can be controlled, a liquid crystal display device having a polymer layer (hereinafter, also referred to as polymer sustained alignment (PSA) layer) which can control alignment of liquid crystal molecules and which is formed by polymerizing a monomer contained in a liquid crystal composition, a production method preferable for producing the liquid crystal display device and so on.

BACKGROUND ART

A liquid crystal display (LCD) device is an appliance capable of controlling transmission/blocking of light (on/off of display) by controlling alignment of liquid crystal molecules having birefringence. There are, as a liquid crystal alignment mode of LCD, a twisted nematic (TN) mode in which liquid crystal molecules having positive anisotropy of dielectric constant are aligned while being twisted at 90° in observation of the liquid crystal molecules from the normal direction of a substrate; a vertical alignment (VA) mode in which liquid crystal molecules having negative anisotropy of dielectric constant are aligned vertically to a substrate face; and an in-plane switching (IPS) or fringe field switching (FFS) mode in which liquid crystal molecules having positive or negative anisotropy of dielectric constant are aligned horizontally to a substrate face and a transverse electric field is applied; etc.

In the vertical alignment mode, the initial alignment of liquid crystal molecules is orthogonal to a substrate face. A method for forming a vertical alignment film on a substrate face of a liquid crystal display device is the mainstream as a method for aligning liquid crystal molecules vertically to a substrate face.

Further, in recent years, a technique for forming a polymer layer (PSA layer) capable of controlling alignment of liquid crystal molecules on an alignment film or on a substrate having no alignment film has drawn attention. A PSA layer is formed by sealing a liquid crystal composition obtained by mixing a polymerizable component such as a monomer, an oligomer, or the like (hereinafter, referred to as monomer or the like for short) with a liquid crystal material between substrates and polymerizing the monomer or the like by heat or light (e.g. ultraviolet) irradiation. The alignment of liquid crystal molecules can be held by such a polymer layer.

Patent Document 1 discloses a liquid crystal display device having no alignment film but a hardened resin layer formed by light irradiation after liquid crystal injection instead. This resin layer is formed by injecting a liquid crystal into an intermediate product of a liquid crystal display panel and thereafter hardening a curable resin containing a monofunctional monomer and a polyfunctional monomer in combination and the functional groups capable of exhibiting vertical alignment of molecules composing the curable resin are generated while being tilted at almost a constant angle to the surface of a substrate to vertically align liquid crystal molecules.

CITATION LIST

Patent Literature

Patent Literature 1: JP 2004-184846 A

SUMMARY OF INVENTION

Technical Problem

Inventors of the present invention made investigations and found that there was a case that good display could not be obtained in accordance with materials to be used and production conditions to be employed even if a liquid crystal composition containing a liquid crystal material, a monomer, a polymerization initiator, etc. was injected between a pair of substrates and a polymer layer was formed by causing polymerization reaction in prescribed condition.

In Patent Document 1, use of a polyfunctional monomer having a lower alkyl group as a monomer for forming a polymer layer is investigated. However, on the basis of investigations which the inventors of the present invention made, it was made clear that the monomer disclosed in Patent Document 1 had weak intermolecular interaction with liquid crystal molecules and was difficult to be aligned vertically to the substrate face since the carbon number of the alkyl group was small.

The inventors of the present invention made further investigations on other monomers for forming a polymer layer and found that lauryl acrylate represented by the following formula (35) had alkyl with 12 carbon atoms and was capable of aligning liquid crystal molecules vertically to the substrate face, but lauryl acrylate caused alignment defects such as light spots and bright lines, and decrease of voltage holding ratio (VHR).

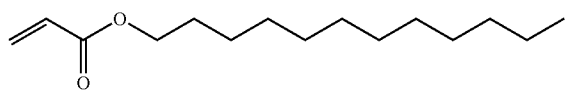

(35)

Some of aspects of the present invention have made in view of the above state of the art and it is an object in an aspect of the present invention to provide a monomer and a liquid crystal composition capable of forming a polymer layer for maintaining high voltage holding ratio, a liquid crystal display device capable of maintaining high voltage holding ratio, and a production method for a liquid crystal display device capable of maintaining high voltage holding ratio.

Solution to Problem

Inventors of the present invention has made various investigations on a cause to decrease voltage holding ratio (VHR) and found that a radical polymerizable monomer generated a radical by ultraviolet irradiation and was polymerized to form a polymer layer, whereas lauryl acrylate had only one polymerizable group and therefore the polymerization speed was decreased and the radical generated in the polymerizable group at the polymerization terminal remained as an impurity in a liquid crystal layer to cause decrease of voltage holding ratio (VHR).

The inventors of the present invention have made investigations on a monomer which could stabilize alignment of liquid crystal molecules and could keep high voltage holding ratio and found that liquid crystal molecules could be aligned vertically to the substrate face and high voltage holding ratio (VHR) could be maintained by using a radical polymerizable monomer formed by bonding a hydrocarbon group with 12 carbon atoms or more to a compound formed by bonding two polymerizable groups to a cyclic aliphatic compound or an aromatic compound with 6 carbon atoms or more.

As a result, the inventors of the present invention can solve the above-mentioned problem and these findings have now led to completion in an aspect of the present invention.

One aspect of the present invention is a liquid crystal composition containing a liquid crystal material and one or more kind monomers, of which at least one of the monomers is a compound formed by further bonding a hydrocarbon group with 12 carbon atoms or more to a compound formed by bonding two polymerizable groups to a cyclic aliphatic compound or an aromatic compound with 6 carbon atoms or more.

A carbon atom of the above-mentioned cyclic aliphatic compound or aromatic compound with 6 carbon atoms or more may be substituted with one or more oxygen atoms, nitrogen atoms, or sulfur atoms.

The above-mentioned cyclic aliphatic compound or aromatic compound with 6 carbon atoms or more and two polymerizable groups may be bonded directly to each other or through an atomic group. Examples of the atomic group may include $Sp^1$, $R^1$, $Sp^2$, and $R^2$ as described later. A compound formed by bonding two polymerizable groups to a cyclic aliphatic compound or an aromatic compound with 6 carbon atoms or more and a hydrocarbon group with 12 carbon atoms or more may be bonded directly to each other or through an atomic group. Examples of the atomic group may include $Z^2$ and $Z^3$ as described later.

The above-mentioned one or more kind monomers are polymerized to form a polymer layer by which alignment of liquid crystal molecules can be controlled. Further, since having a hydrocarbon group with 12 carbon atoms or more, the monomers can stably control alignment of liquid crystal molecules by strong intermolecular interaction with the liquid crystal molecules. Further, since having two polymerizable groups, the monomers are easy to be taken in a polymer layer when the polymer layer is formed and hardly remain as an impurity in a liquid crystal layer and consequently hardly lower the voltage holding ratio (VHR).

The above-mentioned compound formed by further bonding a hydrocarbon group with 12 carbon atoms or more to a compound formed by bonding two polymerizable groups to a cyclic aliphatic compound or an aromatic compound with 6 carbon atoms or more is preferable to be a compound represented by the following formula (1).

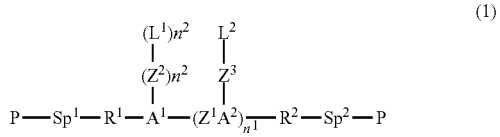

(1)

in the formula,

P denotes the same or different radical polymerizable group;

$Sp^1$ and $Sp^2$ may be the same or different, and respectively denote a straight, branched or cyclic alkylene or alkyleneoxy group with 1 to 6 carbon atoms, or a direct bond;

$R^1$ and $R^2$ may be the same or different, and denote —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, —CO—CH=CH— groups, or a direct bond;

a hydrogen atom included in $R^1$ and $R^2$ may be substituted with a fluorine atom or a chlorine atom;

a —CH$_2$— group included in $R^1$ and $R^2$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, or —OCO—CH=CH— groups unless an oxygen atom and a sulfur atom neighbor each other;

$A^1$ and $A^2$ may be the same or different, and denote a trivalent alicyclic, aromatic monocyclic, or condensed polycyclic hydrocarbon group;

a —CH$_2$— group of $A^1$ and $A^2$ may be substituted with an —O— or a —S— group unless neighboring each other;

a —CH= group included in $A^1$ and $A^2$ may be substituted with a —N= group unless neighboring each other;

a hydrogen atom of included in $A^1$ and $A^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;

$Z^1$, $Z^2$, and $Z^3$ may be the same or different, and denote —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —NHCO—, —N(CH$_3$)CO—, —N(C$_2$H$_5$)CO—, —N(C$_3$H$_7$)CO—, —N(C$_4$H$_9$)CO—, —CONH—, —CON(CH$_3$)—, —CON(C$_2$H$_5$)—, —CON(C$_3$H$_7$)—, —CON(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, —OCO—CH=CH— groups, or a direct bond;

$L^1$ and $L^2$ may be the same or different and an alkyl, an alkenyl, or an aralkyl group with 12 carbon atoms or more, or a monovalent monocyclic or polycyclic hydrocarbon group; the alkyl and alkenyl groups may be straight or branched; one or more hydrogen atoms included in the aralkyl and the monovalent monocyclic or polycyclic hydrocarbon group may be substituted with a straight or branched alkyl or alkenyl group with 1 to 8 carbon atoms;

a —CH$_2$— group included in the alkyl, the alkenyl, and the monovalent monocyclic or polycyclic hydrocarbon group for $L^1$ and $L^2$ may be substituted with —O—, —CO—, —COO—, —OCO—, —O—COO—, —OCH$_2$—, —CH$_2$O—, —C≡C—, —CH=CH—COO— or —OCO—CH=CH— groups unless oxygen atoms neighbor each other;

$n^1$ is 0, 1, or 2; $n^2$ is 0 or 1; and a total of $n^1$ and $n^2$ is 1 to 3.

The above-mentioned compound formed by further bonding a hydrocarbon group with 12 carbon atoms or more to a compound formed by bonding two polymerizable groups to a cyclic aliphatic compound or an aromatic compound with 6 carbon atoms or more is preferable to be a compound represented by the following formula (2).

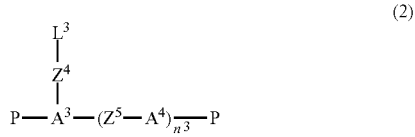

(2)

in the formula,

P denotes the same or different radical polymerizable group;

$A^3$ denotes a trivalent alicyclic, aromatic monocyclic, or condensed polycyclic hydrocarbon group;

$A^4$ denotes a phenylene group;

a —CH$_2$— group included in $A^3$ and $A^4$ may be substituted with an —O— or a —S— group unless neighboring each other;

a —CH═ group included in $A^3$ and $A^4$ may be substituted with a —N═ group unless neighboring each other;

a hydrogen atom of $A^3$ and $A^4$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;

$Z^4$ and $Z^5$ may be the same or different, and denote —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —NHCO—, —N(CH$_3$)CO—, —N(C$_2$H$_5$)CO—, —N(C$_3$H$_7$)CO—, —N(C$_4$H$_9$)CO—, —CONH—, —CON(CH$_3$)—, —CON(C$_2$H$_5$)—, —CON(C$_3$H$_7$)—, —CON(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, —OCO—CH═CH— groups, or a direct bond;

$L^3$ denotes an alkyl, an alkenyl, or an aralkyl with 12 carbon atoms or more, or a monovalent monocyclic or polycyclic hydrocarbon group; the alkyl and alkenyl group may be straight or branched; one or more hydrogen atoms included in the aralkyl and the monovalent monocyclic or polycyclic hydrocarbon group may be substituted with a straight or branched alkyl or alkenyl group with 1 to 8 carbon atoms;

a —CH$_2$— group included in the alkyl, the alkenyl, and the monovalent monocyclic or polycyclic hydrocarbon group for $L^3$ may be substituted with —O—, —CO—, —COO—, —OCO—, —O—COO—, —OCH$_2$—, —CH$_2$O—, —C≡C—, —CH═CH—COO—, or —OCO—CH═CH— group unless oxygen atoms neighbor each other; and $n^3$ denotes 0 or 1.

The trivalent alicyclic, aromatic monocyclic, and condensed polycyclic hydrocarbon group included in $A^1$, $A^2$, and $A^3$ of a compound represented by the formulas (1) and (2) is preferable to be benzene-1,2,3-triyl, benzene-1,2,4-triyl, benzene-1,3,5-triyl, pyridine-2,3,4-triyl, pyridine-2,3,5-triyl, pyridine-2,4,6-triyl, naphthalene-1,2,5-triyl, naphthalene-1,2,6-triyl, naphthalene-1,2,7-triyl, naphthalene-1,2,8-triyl, naphthalene-1,3,5-triyl, naphthalene-1,3,6-triyl, naphthalene-1,3,7-triyl, naphthalene-1,3,8-triyl, naphthalene-1,4,5-triyl, naphthalene-1,4,6-triyl, naphthalene-1,4,7-triyl, naphthalene-1,6,7-triyl, naphthalene-1,6,8-triyl, naphthalene-2,3,6-triyl, cyclohexane-1,2,3-triyl, cyclohexane-1,2,4-triyl, cyclohexane-1,3,5-triyl, decahydronaphthalene-1,2,5-triyl, decahydronaphthalene-1,2,6-triyl, decahydronaphthalene-1,2,7-triyl, decahydronaphthalene-1,2,8-triyl, decahydronaphthalene-1,3,5-triyl, decahydronaphthalene-1,3,6-triyl, decahydronaphthalene-1,3,7-triyl, decahydronaphthalene-1,3,8-triyl, decahydronaphthalene-1,4,5-triyl, decahydronaphthalene-1,4,6-triyl, decahydronaphthalene-1,4,7-triyl, decahydronaphthalene-1,6,7-triyl, decahydronaphthalene-1,6,8-triyl, decahydronaphthalene-2,3,6-triyl, indan-1,1,5-triyl, indan-1,1,6-triyl, indan-1,3,5-triyl, indan-1,3,6-triyl, phenanthrene-1,2,6-triyl, phenanthrene-1,2,7-triyl, phenanthrene-1,2,8-triyl, phenanthrene-1,2,9-triyl, phenanthrene-1,3,6-triyl, phenanthrene-1,3,7-triyl, phenanthrene-1,3,8-triyl, phenanthrene-1,3,9-triyl, phenanthrene-1,6,7-triyl, phenanthrene-1,6,9-triyl, phenanthrene-1,7,9-triyl, phenanthrene-1,8,9-triyl, phenanthrene-1,9,10-triyl, phenanthrene-2,3,6-triyl, phenanthrene-2,3,7-triyl, phenanthrene-2,3,9-triyl, phenanthrene-2,7,9-triyl, phenanthrene-2,9,10-triyl, phenanthrene-3,6,7-triyl, phenanthrene-3,6,9-triyl, phenanthrene-3,9,10-triyl, anthracene-1,2,5-triyl, anthracene-1,2,6-triyl, anthracene-1,2,7-triyl, anthracene-1,2,8-triyl, anthracene-1,2,9-triyl, anthracene-1,2,10-triyl, anthracene-1,3,5-triyl, anthracene-1,3,6-triyl, anthracene-1,3,7-triyl, anthracene-1,3,8-triyl, anthracene-1,3,9-triyl, anthracene-1,3,10-triyl, anthracene-1,4,5-triyl, anthracene-1,4,6-triyl, anthracene-1,4,8-triyl, anthracene-1,4,9-triyl, anthracene-1,5,9-triyl, anthracene-1,6,7-triyl, anthracene-1,6,9-triyl, anthracene-1,7,9-triyl, anthracene-1,8,9-triyl, anthracene-1,9,10-triyl, anthracene-2,3,6-triyl, anthracene-2,3,9-triyl, anthracene-2,6,9-triyl, anthracene-2,7,9-triyl, anthracene-2,7,10-triyl, or anthracene-2,9,10-triyl group.

The phenylene group described in $A^4$ is preferably benzene-1,2-diyl, benzene-1,3-diyl, or benzene-1,4-diyl group.

The above-mentioned compound formed by further bonding a hydrocarbon group with 12 carbon atoms or more to a compound formed by bonding two polymerizable groups to a cyclic aliphatic compound or an aromatic compound with 6 carbon atoms or more is preferable to be a compound represented by one of the following formulas (3-1) to (3-5).

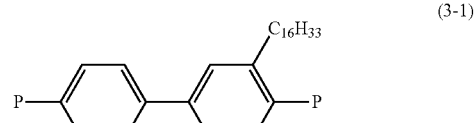

(3-1)

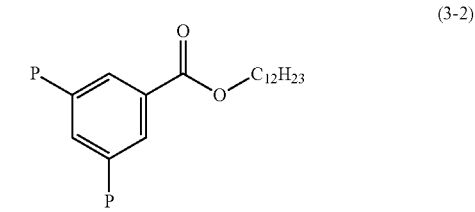

(3-2)

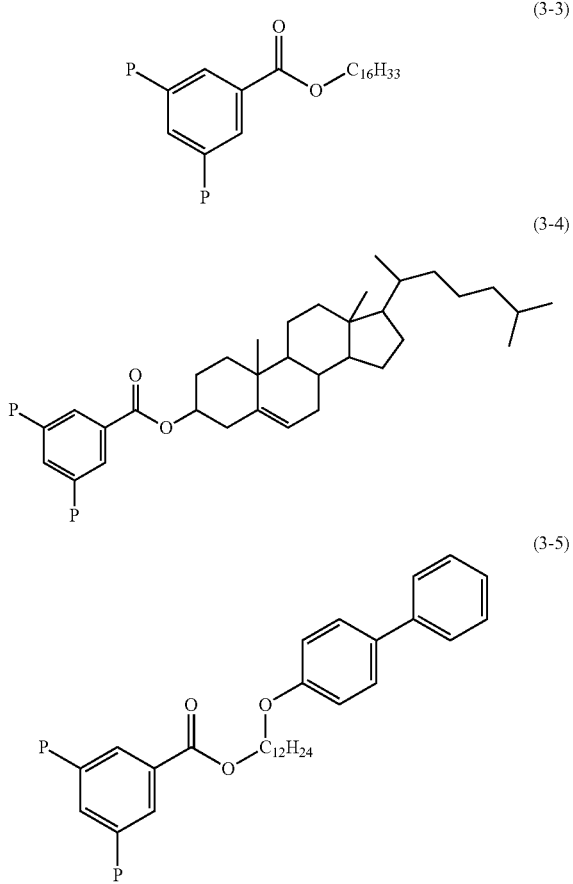

(3-3)

(3-4)

(3-5)

in the formula, P denotes the same or different radical polymerizable group.

The above-mentioned liquid crystal composition is preferable to further contain a monomer having a structure for producing a radical by light irradiation. Use of such a monomer can promote polymerization reaction with no need of newly adding a polymerization initiator and prevent decrease of voltage holding ratio (VHR).

Since there is an example that the structure in the inside of a panel of a liquid crystal display device is deteriorated by irradiation of light with a wavelength component around 300 nm for a long time and the capability of the display device is lowered, in terms of quality retention, it is effective to shorten the light irradiation time needed for polymerization reaction by using the above-mentioned monomer having a structure for producing a radical by light irradiation in combination. Further, the above-mentioned monomer having a structure for producing a radical by light irradiation is preferable to have a structure for efficiently generating a radical by irradiating light having a wavelength component of 300 nm or longer and more preferably 350 nm or longer.

The above-mentioned monomer having a structure for producing a radical by light irradiation is preferable to be a compound represented by the following formula (4) and having a structure for producing a radical by hydrogen abstraction reaction by light irradiation.

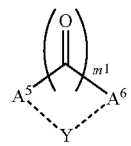

(4)

in the formula,
$A^5$ denotes an aromatic ring;
$A^6$ denotes an aromatic ring same as or different from $A^5$, or a straight or branched alkyl or alkenyl group with 1 to 12 carbon atoms;
at least one of $A^5$ and $A^6$ contains -$Sp^3$-P group;
an aromatic ring included in at least one of $A^5$ and $A^6$ is a benzene ring or a biphenyl ring;
a hydrogen atom included in $A^5$ and $A^6$ may be substituted with -$Sp^3$-P group, a halogen atom, —CN, —NO$_2$, —NCO, —NCS, —OCN, —SCN, —SF$_5$, or an alkyl, an alkenyl or an aralkyl group with 1 to 12 carbon atoms and the alkyl and alkenyl group may be straight or branched;
two neighboring hydrogen atoms included in $A^5$ and $A^6$ may be substituted with a straight or branched alkylene or alkenylene group with 1 to 12 carbon atoms to form a ring structure;
a hydrogen atom included in the alkyl, the alkenyl, the alkylene, the alkenylene or the aralkyl group of $A^5$ and $A^6$ may be substituted with -$Sp^3$-P group;
a —CH$_2$— group included in the alkyl, the alkenyl, the alkylene, the alkenylene or the aralkyl group of $A^5$ and $A^6$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, or —OCO—CH=CH— group unless an oxygen atom, a sulfur atom, and a nitrogen atom neighbor one another;
P denotes a radical polymerizable group;
$Sp^3$ denotes a straight, branched or cyclic alkylene or alkyleneoxy group with 1 to 6 carbon atoms, or a direct bond;
$m^1$ denotes 1 or 2;
a dotted line part connecting $A^5$ and Y and a dotted line part connecting $A^6$ and Y represent that a bond through Y may exist between $A^5$ and $A^6$; and
Y denotes —CH$_2$—, —CH$_2$CH$_2$—, —CH=CH—, —O—, —S—, —NH—, —N(CH$_3$)—, —N(C$_2$H$_5$)—, —N(C$_3$H$_7$)—, —N(C$_4$H$_9$)—, —OCH$_2$—, —CH$_2$O—, —SCH$_2$—, —CH$_2$S—, or a direct bond.

A compound represented by the above-mentioned formula (4) is preferable to be a compound represented by one of the following formulas (6-1) to (6-8);

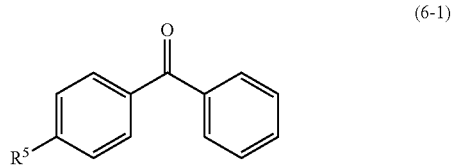

(6-1)

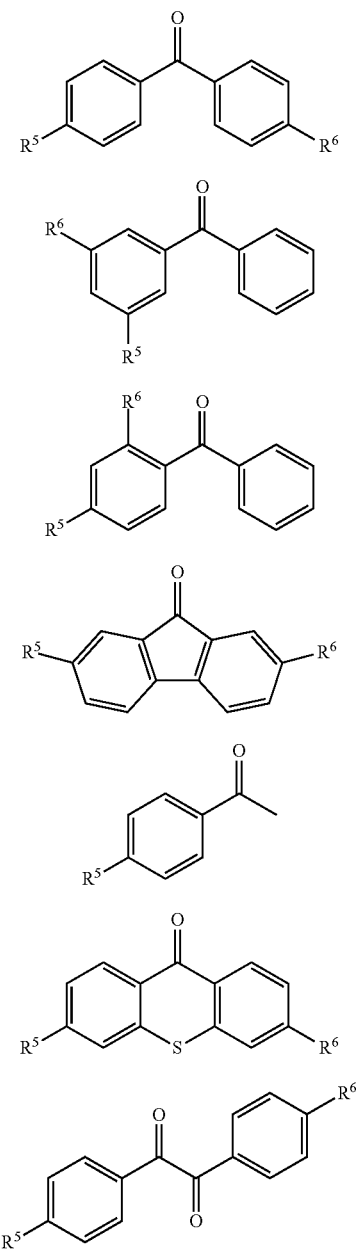

—OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, or —OCO—CH=CH— group unless an oxygen atom, a sulfur atom, and a nitrogen atom neighbor one another.

A compound represented by the above-mentioned formulas (4) and (6-1) to (6-8) produces a radical by hydrogen abstraction reaction by light irradiation and therefore, it is no need to newly add a polymerization initiator. Further, since having polymerizable groups, the compound is easy to be taken in a polymer layer when the polymer layer is formed and hardly remains as an impurity in a liquid crystal layer and consequently hardly lowers the voltage holding ratio (VHR).

A compound having a structure represented by one of the above-mentioned formulas (6-1) to (6-6) has an absorption wavelength region up to around 380 nm and a compound represented by the above-mentioned formula (6-7) or (6-8) has an absorption wavelength region up to around 430 nm. Accordingly, use of a compound having a structure represented by one of the above-mentioned formulas (6-1) to (6-8) in combination can increase the polymerization reaction speed by light irradiation and can improve the throughput in production of a liquid crystal display device even if light with short wavelength (e.g. light with wavelength shorter than 300 nm) is cut. Further, since having a wider light absorption wavelength region than that of a compound having a structure represented by one of the above-mentioned formulas (6-1) to (6-6) to increase the light utilization efficiency, a compound represented by the formula (6-7) or (6-8) is capable of polymerizing a radical polymerizable monomer by light irradiation even after a polarizing plate is respectively stuck to a pair of substrates of a liquid crystal display device.

The above-mentioned monomer having a structure for forming a radical by light irradiation is preferable to be a compound represented by the following formula (5) and having a structure for producing a radical by self-cleavage reaction by light irradiation.

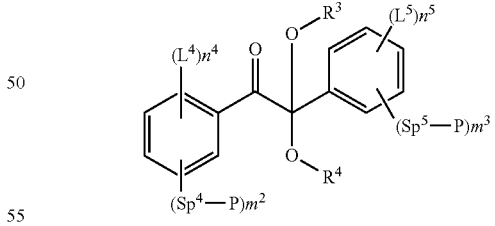

(5)

in the formula,

R$^3$ denotes a straight or branched alkyl or alkenyl group with 1 to 4 carbon atoms or -Sp$^6$-P;

R$^4$ denotes a straight or branched alkyl or alkenyl group with 1 to 4 carbon atoms or -Sp$^7$-P;

P denotes the same or different radical polymerizable group and a total number is 2 or more;

Sp$^4$ denotes a straight, branched, or cyclic alkylene, alkyleneoxy, or alkylenecarbonyloxy group with 1 to 6 carbon atoms, or a direct bond and may be the same or different in the case where m$^2$ is 2 or more;

in the formula,

R$^5$ and R$^6$ may be the same or different, and denote a -Sp$^8$-P group, a hydrogen atom, a halogen atom, —CN, —NO$_2$, —NCO, —NCS, —OCN, —SCN, —SF$_5$, or a straight or branched alkyl or aralkyl with 1 to 12 carbon atoms, or phenyl group;

at least one of R$^5$ and R$^6$ contains -Sp$^8$-P group;

P denotes a radical polymerizable group;

Sp$^8$ denotes a straight, branched or cyclic alkylene or alkyleneoxy group with 1 to 6 carbon atoms, or a direct bond;

in the case where at least one of R$^5$ and R$^6$ is an alkyl or an aralkyl group with 1 to 12 carbon atoms or phenyl group, a hydrogen atom included in R$^5$ and R$^6$ may be substituted with a fluorine atom, a chlorine atom, or -Sp$^8$-P group; and a —CH$_2$— group included in R$^5$ and R$^6$ may be substituted with —O—, —S—, —NH—, —CO—, —COO—, Sp$^5$ denotes a straight, branched, or cyclic alkylene, alkyleneoxy, or alkylenecarbonyloxy group with 1 to 6 carbon atoms, or a direct bond and may be the same or different in the case where m$^3$ is 2 or more;

Sp$^6$ denotes a straight, branched, or cyclic alkylene, alkyleneoxy, or alkylenecarbonyloxy group with 1 to 6 carbon atoms;

Sp$^7$ denotes a straight, branched, or cyclic alkylene, alkyleneoxy, or alkylenecarbonyloxy group with 1 to 6 carbon atoms;

L$^4$ denotes —F, —OH, or a straight or branched alkyl, straight or branched alkenyl, or aralkyl group with 1 to 12 carbon atoms and may be the same or different in the case where n$^4$ is 2 or more;

in the case where two L$^4$s are bonded to two neighboring carbon atoms in an aromatic ring, a ring structure may be formed by bonding each other and the two L$^4$s may be the same or different and be a straight or branched alkylene or alkenylene group with 1 to 12 carbon atoms;

L$^5$ denotes —F, —OH, or a straight or branched alkyl, straight or branched alkenyl, or aralkyl group with 1 to 12 carbon atoms and may be the same or different in the case where n$^5$ is 2 or more;

in the case where two L$^5$s are bonded to two neighboring carbon atoms in an aromatic ring, a ring structure may be formed by bonding each other and the two L$^5$s may be the same or different and be a straight or branched alkylene or alkenylene group with 1 to 12 carbon atoms;

one or more hydrogen atoms included in the alkyl, the alkenyl, the alkylene, the alkenylene or the aralkyl of L$^4$ and L$^5$ may be substituted with —F or —OH group;

a —CH$_2$— group included in the alkyl, the alkenyl, the alkylene, the alkenylene or the aralkyl group of L$^4$ and L$^5$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, —OCO—CH═CH—, -Sp$^4$-P, or -Sp$^5$-P group unless an oxygen atom, a sulfur atom, and a nitrogen atom neighbor one another;

m$^2$ denotes an integer of 1 to 3;
m$^3$ denotes an integer of 0 to 3;
n$^4$ denotes an integer of 0 to 4;
n$^5$ denotes an integer of 0 to 4;
a total of m$^2$ and n$^4$ is an integer of 1 to 5;
a total of m$^3$ and n$^5$ is an integer of 0 to 5; and
a total of m$^2$ and m$^3$ is an integer of 1 to 6.

A compound represented by the above-mentioned formula (5) is preferable to be a compound represented by the following formula (7);

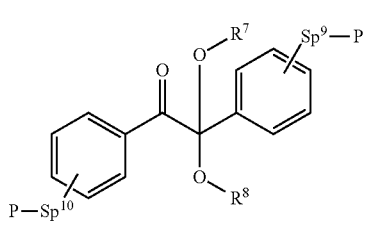

(7)

in the formula,
R$^7$ denotes a straight or branched alkyl or alkenyl group with 1 to 4 carbon atoms;
R$^8$ denotes a straight or branched alkyl or alkenyl group with 1 to 4 carbon atoms;
P denotes the same or different radical polymerizable group;
Sp$^9$ denotes a straight, branched, or cyclic alkylene, alkyleneoxy, or alkylenecarbonyloxy group with 1 to 6 carbon atoms, or a direct bond; and
Sp$^{10}$ denotes a straight, branched, or cyclic alkylene, alkyleneoxy, or alkylenecarbonyloxy group with 1 to 6 carbon atoms, or a direct bond.

A compound represented by the above-mentioned formulas (5) and (7) produces a radical by self-cleavage reaction by light irradiation and therefore, it is no need to newly add a polymerization initiator. Further, since having polymerizable groups, the compound is easy to be taken in a polymer layer when the polymer layer is formed and hardly remains as an impurity in a liquid crystal layer and consequently hardly lowers the voltage holding ratio (VHR).

P contained in a compound represented by the above-mentioned formulas (1) to (7) is preferable to be (meth)acryloyloxy, (meth)acryloylamino, vinyl, or vinyloxy group.

A monomer in an aspect of the present invention is a compound represented by the above-mentioned formula (1). A monomer in an aspect of the present invention is also a compound represented by the above-mentioned formula (2).

The present invention also provides a liquid crystal display device produced preferably by using the above-mentioned liquid crystal composition.

Another aspect of the present invention is a liquid crystal display device which has a pair of substrates; a liquid crystal layer sandwiched between the pair of the substrates and containing a liquid crystal material; and a polymer layer formed on at least one of the pair of the substrates and configured to control alignment of liquid crystal molecules, in which the polymer layer is formed by polymerizing one or more kind monomers and at least one of the monomers is a compound formed by further bonding a hydrocarbon group with 12 carbon atoms or more to a compound formed by bonding two polymerizable groups to a cyclic aliphatic compound or an aromatic compound with 6 carbon atoms or more. The polymer layer may be formed by polymerizing one or more kind monomers added to the liquid crystal layer.

A carbon atom of the above-mentioned cyclic aliphatic compound or aromatic compound with 6 carbon atoms or more may be substituted with one or more oxygen atoms, nitrogen atoms, or sulfur atoms.

The above-mentioned cyclic aliphatic compound or aromatic compound with 6 carbon atoms or more and two polymerizable groups may be bonded directly to each other or through an atomic group. Examples of the atomic group may include Sp$^1$, R$^1$, Sp$^2$, and R$^2$ as described later. A compound produced by bonding two polymerizable groups to a cyclic aliphatic compound or an aromatic compound with 6 carbon atoms or more and a hydrocarbon group with 12 carbon atoms or more may be bonded directly to each other or through an atomic group. Examples of the atomic group may include Z$^2$ and Z$^3$ as described later.

A pair of substrates comprised in a liquid crystal display device in an aspect of the present invention is used, for example, in one of them as an array substrate and the other as a color filter substrate. The array substrate is provided with a plurality of pixel electrodes and accordingly, liquid crystal alignment can be controlled for every pixel unit. In the color filter substrate, a plurality of color filters are arranged at positions where the pixel electrodes of the array substrate are respectively overlapped to control the display colors for every pixel unit.

A polymer layer for controlling alignment of liquid crystal molecules is formed on at least one substrate of the above-mentioned pair of substrates and the polymer layer is formed by polymerizing one or more kind monomers. Formation of the above-mentioned polymer layer makes it possible to control the initial tilt of the liquid crystal molecules close to the polymer layer in a constant direction. For example, in the case where a polymer layer is formed by polymerizing a monomer in a state that liquid crystal molecules are aligned while being pre-tilted, the polymer layer is to be formed in a manner of having a structure for aligning the liquid crystal molecules by pre-tilt alignment.

Further, since at least one of the above-mentioned monomers has a hydrocarbon group with 12 carbon atoms or more, the polymer layer can align liquid crystal molecules vertically to the substrate face by strong intermolecular interaction with the liquid crystal molecules.

As long as being formed by indispensably using these constituent elements, the configuration of the liquid crystal display device in an aspect of the present invention is not particularly limited by other constituent elements.

Examples as a preferable aspect of the liquid crystal display device in an aspect of the present invention are the following aspects (a) to (j) same as the contents described for a preferable aspects of the liquid crystal composition in an aspect of the present invention. That is, (a) an aspect in which a compound formed by further bonding a hydrocarbon group with 12 carbon atoms or more to a compound formed by bonding two polymerizable groups to a cyclic aliphatic compound or an aromatic compound with 6 carbon atoms or more is a compound represented by the above-mentioned formula (1):

(b) an aspect in which a compound formed by further bonding a hydrocarbon group with 12 carbon atoms or more to a compound formed by bonding two polymerizable groups to a cyclic aliphatic compound or an aromatic compound with 6 carbon atoms or more is a compound represented by the above-mentioned formula (2):

(c) an aspect in which the trivalent alicyclic, aromatic monocyclic, and condensed polycyclic hydrocarbon group of compounds $A^1$, $A^2$, and $A^3$ represented by the above-mentioned formulas (1) and (2) is benzene-1,2,3-triyl, benzene-1,2,4-triyl, benzene-1,3,5-triyl, pyridine-2,3,4-triyl, pyridine-2,3,5-triyl, pyridine-2,4,6-triyl, naphthalene-1,2,5-triyl, naphthalene-1,2,6-triyl, naphthalene-1,2,7-triyl, naphthalene-1,2,8-triyl, naphthalene-1,3,5-triyl, naphthalene-1,3,6-triyl, naphthalene-1,3,7-triyl, naphthalene-1,3,8-triyl, naphthalene-1,4,5-triyl, naphthalene-1,4,6-triyl, naphthalene-1,4,7-triyl, naphthalene-1,6,7-triyl, naphthalene-1,6,8-triyl, naphthalene-2,3,6-triyl, cyclohexane-1,2,3-triyl, cyclohexane-1,2,4-triyl, cyclohexane-1,3,5-triyl, decahydronaphthalene-1,2,5-triyl, decahydronaphthalene-1,2,6-triyl, decahydronaphthalene-1,2,7-triyl, decahydronaphthalene-1,2,8-triyl, decahydronaphthalene-1,3,5-triyl, decahydronaphthalene-1,3,6-triyl, decahydronaphthalene-1,3,7-triyl, decahydronaphthalene-1,3,8-triyl, decahydronaphthalene-1,4,5-triyl, decahydronaphthalene-1,4,6-triyl, decahydronaphthalene-1,4,7-triyl, decahydronaphthalene-1,6,7-triyl, decahydronaphthalene-1,6,8-triyl, decahydronaphthalene-2,3,6-triyl, indan-1,1,5-triyl, indan-1,1,6-triyl, indan-1,3,5-triyl, indan-1,3,6-triyl, phenanthrene-1,2,6-triyl, phenanthrene-1,2,7-triyl, phenanthrene-1,2,8-triyl, phenanthrene-1,2,9-triyl, phenanthrene-1,3,6-triyl, phenanthrene-1,3,7-triyl, phenanthrene-1,3,8-triyl, phenanthrene-1,3,9-triyl, phenanthrene-1,6,7-triyl, phenanthrene-1,6,9-triyl, phenanthrene-1,7,9-triyl, phenanthrene-1,8,9-triyl, phenanthrene-1,9,10-triyl, phenanthrene-2,3,6-triyl, phenanthrene-2,3,7-triyl, phenanthrene-2,3,9-triyl, phenanthrene-2,7,9-triyl, phenanthrene-2,9,10-triyl, phenanthrene-3,6,7-triyl, phenanthrene-3,6,9-triyl, phenanthrene-3,9,10-triyl, anthracene-1,2,5-triyl, anthracene-1,2,6-triyl, anthracene-1,2,7-triyl, anthracene-1,2,8-triyl, anthracene-1,2,9-triyl, anthracene-1,2,10-triyl, anthracene-1,3,5-triyl, anthracene-1,3,6-triyl, anthracene-1,3,7-triyl, anthracene-1,3,8-triyl, anthracene-1,3,9-triyl, anthracene-1,3,10-triyl, anthracene-1,4,5-triyl, anthracene-1,4,6-triyl, anthracene-1,4,8-triyl, anthracene-1,4,9-triyl, anthracene-1,5,9-triyl, anthracene-1,6,7-triyl, anthracene-1,6,9-triyl, anthracene-1,7,9-triyl, anthracene-1,8,9-triyl, anthracene-1,9,10-triyl, anthracene-2,3,6-triyl, anthracene-2,3,9-triyl, anthracene-2,6,9-triyl, anthracene-2,7,9-triyl, anthracene-2,7,10-triyl, or anthracene-2,9,10-triyl group: an aspect in which the phenylene for $A^4$ is benzene-1,2-diyl, benzene-1,3-diyl, or benzene-1,4-diyl group:

(d) an aspect in which the compound formed by further bonding a hydrocarbon group with 12 carbon atoms or more to a compound formed by bonding two polymerizable groups to a cyclic aliphatic compound or an aromatic compound with 6 carbon atoms or more is a compound represented by one of the above-mentioned formulas (3-1) to (3-5):

(e) an aspect in which the above-mentioned liquid crystal composition contains a monomer having a structure for producing a radical by light irradiation:

(f) an aspect in which the monomer having a structure for producing a radical by light irradiation is a compound represented by the above-mentioned formula (4) and having a structure for producing a radical by hydrogen abstraction reaction by light irradiation:

(g) an aspect in which the compound represented by the above-mentioned formula (4) is a compound represented by one of the above-mentioned formulas (6-1) to (6-8);

(h) an aspect in which the monomer having a structure for forming a radical by light irradiation is a compound represented by the above-mentioned formula (5) and having a structure for producing a radical by self-cleavage reaction by light irradiation:

(i) an aspect in which the compound represented by the above-mentioned formula (5) is a compound represented by the above-mentioned formula (7): and (j) an aspect in which P contained in compounds represented by the above-mentioned formulas (1) to (7) is (meth)acryloyloxy, (meth)acryloylamino, vinyl, or vinyloxy group.

The present invention also provides a production method for a liquid crystal display device for which the above-mentioned liquid crystal composition is used preferably.

Another aspect of the present invention is a production method for a liquid crystal display device which involves injecting a liquid crystal composition containing a liquid crystal material and one or more kind monomers between a pair of substrates; and forming a polymer layer for controlling alignment of liquid crystal molecules on a substrate by polymerizing the monomers by radiating the liquid crystal composition with light and in which at least one of the monomers is a compound formed by further bonding a hydrocarbon group with 12 carbon atoms or more to a compound formed by bonding two polymerizable groups to a cyclic aliphatic compound or an aromatic compound with 6 carbon atoms or more.

A carbon atom of the above-mentioned cyclic aliphatic compound or aromatic compound with 6 carbon atoms or more may be substituted with one or more oxygen atoms, nitrogen atoms, or sulfur atoms.

The above-mentioned cyclic aliphatic compound or aromatic compound with 6 carbon atoms or more and two polymerizable groups may be bonded directly to each other or through an atomic group. Examples of the atomic group may include $Sp^1$, $R^1$, $Sp^2$, and $R^2$ as described later. A compound produced by bonding two polymerizable groups to a cyclic aliphatic compound or an aromatic compound with 6 carbon atoms or more and a hydrocarbon group with 12 carbon atoms or more may be bonded directly to each other or through an atomic group. Examples of the atomic group may include $Z^2$ and $Z^3$ as described later.

A production method for a liquid crystal display device according to the present invention has a step of injecting a liquid crystal composition containing a liquid crystal material and one or more kind monomers between a pair of substrates. Herein, the liquid crystal material and monomers to be used may be the same ones as described in the above-mentioned liquid crystal display device in an aspect of the present invention.

The production method for a liquid crystal display device in an aspect of the present invention has a step of forming a polymer layer for controlling alignment of liquid crystal molecules on a substrate by polymerizing the monomers by irradiating the liquid crystal composition with light. According to the production method in an aspect of the present invention, a liquid crystal display device in which alignment of liquid crystal molecules is controlled and decrease of voltage holding ratio is suppressed can be obtained.

The above-mentioned step for forming the polymer layer may include a step carried out in a state that voltage not lower than the threshold value is not applied to the liquid crystal layer. Even in the state that voltage not lower than the threshold value is not applied, a polymer layer for reinforcing the initial alignment of liquid crystal molecules can be formed.

The above-mentioned step for forming the polymer layer may include a step carried out in a state that voltage not lower than the threshold value is applied to the liquid crystal layer. At the time of carrying out the PSA polymerization step, a polymer is formed following the liquid crystal molecules aligned in the state that voltage not lower than the threshold value is applied to the liquid crystal layer by irradiating light in the state that voltage not lower than the threshold value is applied. Therefore, the polymer layer to be formed is to have a structure for defining the pre-tilt angle to the liquid crystal molecules even in the state that no voltage is applied thereafter.

As long as the production method for a liquid crystal display device in an aspect of the present invention indispensably involves the above-mentioned steps, the production method is not particularly limited by other steps.

Examples as a preferable aspect of the production method for a liquid crystal display device in an aspect of the present invention are the following aspects (k) to (t) same as the contents described as a preferable aspect of the liquid crystal composition in an aspect of the present invention. That is, (k) an aspect in which a compound formed by further bonding a hydrocarbon group with 12 carbon atoms or more to a compound formed by bonding two polymerizable groups to a cyclic aliphatic compound or an aromatic compound with 6 carbon atoms or more is a compound represented by the above-mentioned formula (1):

(l) an aspect in which a compound formed by further bonding a hydrocarbon group with 12 carbon atoms or more to a compound formed by bonding two polymerizable groups to a cyclic aliphatic compound or an aromatic compound with 6 carbon atoms or more is a compound represented by the above-mentioned formula (2):

(m) an aspect in which the trivalent alicyclic, aromatic monocyclic, and condensed polycyclic hydrocarbon group of compounds $A^1$, $A^2$, and $A^3$ represented by the above-mentioned formulas (1) and (2) is benzene-1,2,3-triyl, benzene-1,2,4-triyl, benzene-1,3,5-triyl, pyridine-2,3,4-triyl, pyridine-2,3,5-triyl, pyridine-2,4,6-triyl, naphthalene-1,2,5-triyl, naphthalene-1,2,6-triyl, naphthalene-1,2,7-triyl, naphthalene-1,2,8-triyl, naphthalene-1,3,5-triyl, naphthalene-1,3,6-triyl, naphthalene-1,3,7-triyl, naphthalene-1,3,8-triyl, naphthalene-1,4,5-triyl, naphthalene-1,4,6-triyl, naphthalene-1,4,7-triyl, naphthalene-1,6,7-triyl, naphthalene-1,6,8-triyl, naphthalene-2,3,6-triyl, cyclohexane-1,2,3-triyl, cyclohexane-1,2,4-triyl, cyclohexane-1,3,5-triyl, decahydronaphthalene-1,2,5-triyl, decahydronaphthalene-1,2,6-triyl, decahydronaphthalene-1,2,7-triyl, decahydronaphthalene-1,2,8-triyl, decahydronaphthalene-1,3,5-triyl, decahydronaphthalene-1,3,6-triyl, decahydronaphthalene-1,3,7-triyl, decahydronaphthalene-1,3,8-triyl, decahydronaphthalene-1,4,5-triyl, decahydronaphthalene-1,4,6-triyl, decahydronaphthalene-1,4,7-triyl, decahydronaphthalene-1,6,7-triyl, decahydronaphthalene-1,6,8-triyl, decahydronaphthalene-2,3,6-triyl, indan-1,1,5-triyl, indan-1,1,6-triyl, indan-1,3,5-triyl, indan-1,3,6-triyl, phenanthrene-1,2,6-triyl, phenanthrene-1,2,7-triyl, phenanthrene-1,2,8-triyl, phenanthrene-1,2,9-triyl, phenanthrene-1,3,6-triyl, phenanthrene-1,3,7-triyl, phenanthrene-1,3,8-triyl, phenanthrene-1,3,9-triyl, phenanthrene-1,6,7-triyl, phenanthrene-1,6,9-triyl, phenanthrene-1,7,9-triyl, phenanthrene-1,8,9-triyl, phenanthrene-1,9,10-triyl, phenanthrene-2,3,6-triyl, phenanthrene-2,3,7-triyl, phenanthrene-2,3,9-triyl, phenanthrene-2,7,9-triyl, phenanthrene-2,9,10-triyl, phenanthrene-3,6,7-triyl, phenanthrene-3,6,9-triyl, phenanthrene-3,9,10-triyl, anthracene-1,2,5-triyl, anthracene-1,2,6-triyl, anthracene-1,2,7-triyl, anthracene-1,2,8-triyl, anthracene-1,2,9-triyl, anthracene-1,2,10-triyl, anthracene-1,3,5-triyl, anthracene-1,3,6-triyl, anthracene-1,3,7-triyl, anthracene-1,3,8-triyl, anthracene-1,3,9-triyl, anthracene-1,3,10-triyl, anthracene-1,4,5-triyl, anthracene-1,4,6-triyl, anthracene-1,4,8-triyl, anthracene-1,4,9-triyl, anthracene-1,5,9-triyl, anthracene-1,6,7-triyl, anthracene-1,6,9-triyl, anthracene-1,7,9-triyl, anthracene-1,8,9-triyl, anthracene-1,9,10-triyl, anthracene-2,3,6-triyl, anthracene-2,3,9-triyl, anthracene-2,6,9-triyl, anthracene-2,7,9-triyl, anthracene-2,7,10-triyl, or anthracene-2,9,10-triyl group: an aspect in which the phenylene described in $A^4$ is benzene-1,2-diyl, benzene-1,3-diyl, or benzene-1,4-diyl:

(n) an aspect in which the compound formed by further bonding a hydrocarbon group with 12 carbon atoms or more to a compound formed by bonding two polymerizable groups to a cyclic aliphatic compound or an aromatic compound with 6 carbon atoms or more is a compound represented by one of the above-mentioned formulas (3-1) to (3-5):

(o) an aspect in which the above-mentioned liquid crystal composition contains a monomer having a structure for producing a radical by light irradiation:

(p) an aspect in which the monomer having a structure for producing a radical by light irradiation is a compound represented by the above-mentioned formula (4) and having a structure for producing a radical by hydrogen abstraction reaction by light irradiation:

(q) an aspect in which the compound represented by the above-mentioned formula (4) is a compound represented by one of the above-mentioned formulas (6-1) to (6-8);

(r) an aspect in which the monomer having a structure for producing a radical by light irradiation is a compound represented by the above-mentioned formula (5) and having a structure for producing a radical by self-cleavage reaction by light irradiation:

(s) an aspect in which the compound represented by the above-mentioned formula (5) is a compound represented by the above-mentioned formula (7): and (t) an aspect in which P contained in compounds represented by the above-mentioned formulas (1) to (7) is (meth) acryloyloxy, (meth)acryloylamino, vinyl, or vinyloxy group.

Advantageous Effects of Invention

According to the present invention, it is made possible to obtain a monomer and a liquid crystal composition capable of forming a polymer layer for maintaining high voltage holding ratio, a liquid crystal display device capable of maintaining high voltage holding ratio, and a production method for a liquid crystal display device capable of maintaining high voltage holding ratio.

DESCRIPTION OF EMBODIMENTS

Figure 1:
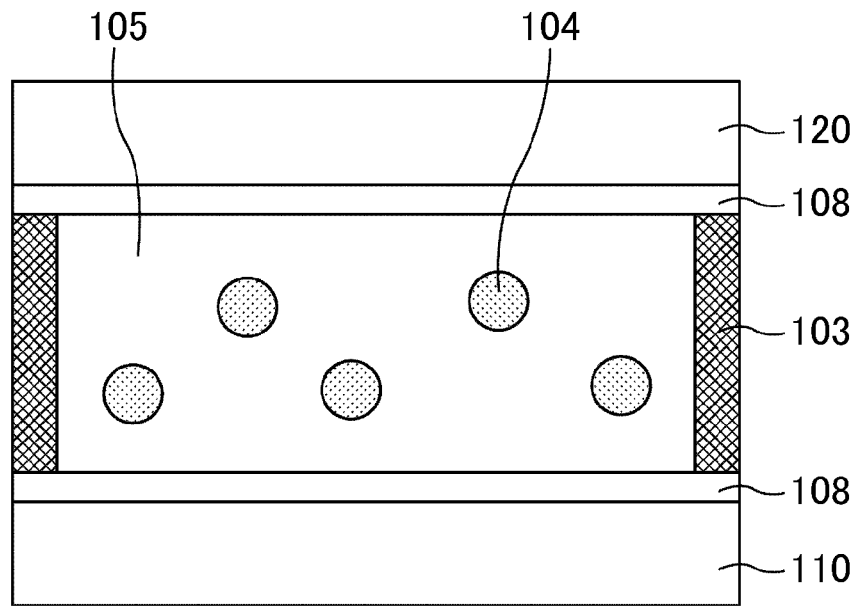
FIG. 1 is a schematic view of a cross section of a liquid crystal display device of Embodiment 1 before a PSA polymerization step.

Hereinafter, the present invention will be described in more detail referring to the drawings in the following embodiments, but is not limited to these embodiments.

Embodiment 1

A liquid crystal display device produced by using a liquid crystal composition in an aspect of the present invention and a liquid crystal display device produced by the production method in an aspect of the present invention exhibit excellent display properties while being used for display devices, for example, a television, a personal computer, a mobile phone, an information display, etc.

Figure 2:
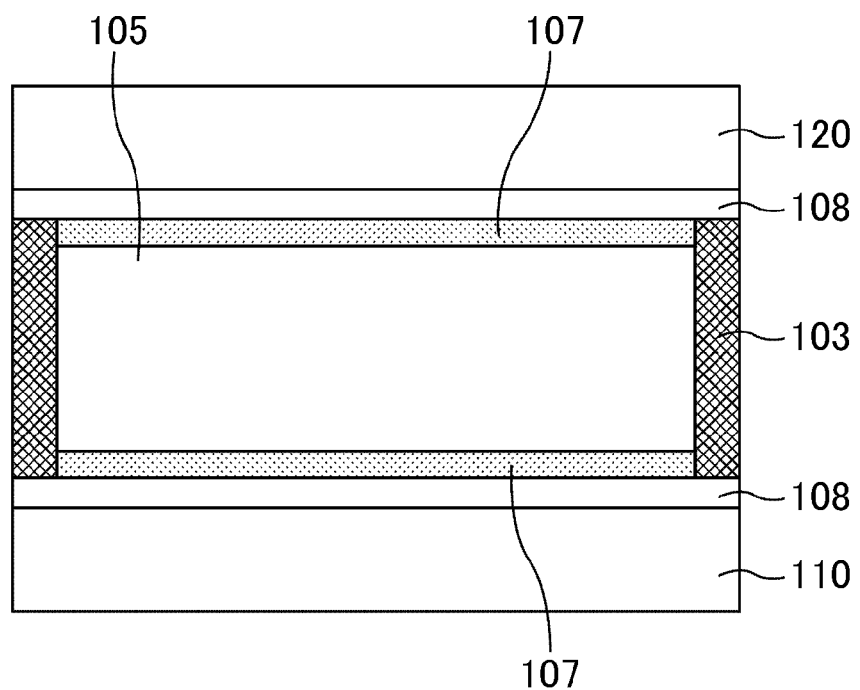
FIG. 2 is a schematic view of a cross section of a liquid crystal display device of Embodiment 1 after the PSA polymerization step.

Hereinafter, one example of a production method of a liquid crystal display device of Embodiment 1 will be described. FIG. 1 and FIG. 2 are schematic cross sectional views of a liquid crystal display device of Embodiment 1 and FIG. 1 illustrates the view before a PSA polymerization step and FIG. 2 illustrates the view after the PSA polymerization step. As illustrated in FIG. 1 and FIG. 2, the liquid crystal display device of Embodiment 1 has an array substrate 110, a color filter substrate 120, and a liquid crystal layer 105 sandwiched between a pair of the substrates, that is, the array substrate 110 and the color filter substrate 120. The array substrate 110 has an insulating transparent substrate made of a material such as glass or the like, and various kinds of wiring, a pixel electrode, and a TFT (thin film transistor) formed on the transparent substrate. The color filter substrate 120 has an insulating transparent substrate made of a material such as glass or the like, and a color filter, a black matrix, and a common electrode formed on the transparent substrate. The array substrate 110 and the color filter substrate 120 are respectively provided with an alignment film 108 on the surfaces having contact with the liquid crystal layer 105.

As illustrated in FIG. 1, before the PSA polymerization step, the liquid crystal layer 105 contains a liquid crystal material and a radical polymerizable monomer 104. The radical polymerizable monomer 104 is a compound formed by further bonding a hydrocarbon group with 12 carbon atoms or more to a compound formed by bonding two polymerizable groups to a cyclic aliphatic compound or an aromatic compound with 6 carbon atoms or more. More practically, the radical polymerizable monomer is a compound represented by the above-mentioned formula (1) and more practically a compound represented by the above-mentioned formula (2) and furthermore practically a compound represented by one of the above-mentioned formula (3-1) to (3-5).

The radical polymerizable monomer 104 produces a radical by irradiating the liquid crystal layer 105 with light and using the radical as active species, the radical polymerizable group of the radical polymerizable monomer 104 successively starts and promotes chain polymerization to be polymerized. The polymer formed by the polymerization is deposited in the form of a polymer layer (PSA layer) 107 on the alignment film 108 formed on the substrates 110 and 120 as illustrated in FIG. 2.

In the case where a common polymerization initiator (e.g. Irgacure 651 or the like) is used, products formed by cleavage by ultraviolet irradiation float as impurities in a liquid crystal and consequently lower the voltage holding ratio (VHR). In Embodiment 1, since producing a radical by itself, the radical polymerizable monomer 104 does not require such a polymerization initiator and does not produce impurities derived from the polymerization initiator and consequently keeps high voltage holding ratio (VHR). Further, since having two polymerizable groups, the radical polymerizable monomer 104 is easy to be taken in a polymer layer 107 when the polymer layer 107 is formed and hardly remains as an impurity in the liquid crystal layer and consequently does not lower the voltage holding ratio (VHR).

As illustrated in FIG. 2, in Embodiment 1, the polymer layer 107 is formed on the surface of the alignment film 108 formed on the array substrate 110 and the color filter substrate 120. Between the array substrate 110 and the color filter substrate 120, a sealing material 103 is stuck to the alignment film 108 along the outer rim of these substrates 110 and 120 and the liquid crystal layer 105 is enclosed between the array substrate 110 and the color filter substrate 120 by the sealing material 103. Radiation of the liquid crystal layer 105 with light is carried out after sealing the liquid crystal layer 105 by the sealing material 103 so that the polymer layer 107 is formed in the region surrounded with the sealing material 103.

In Embodiment 1, at the time of carrying out the PSA polymerization step, a polymer layer can be produced and liquid crystal molecules can be aligned vertically to the substrate face without applying voltage not lower than the threshold value to the liquid crystal layer 105 in the case where one or more kind radical polymerizable monomers are used in Embodiment 1. Further, at the time of carrying out the PSA polymerization step, a polymer is formed following the liquid crystal molecules aligned in the state that voltage not lower than the threshold value is applied to the liquid crystal layer 105 by radiating the liquid crystal layer 105 with light in the state that voltage not lower than the threshold value is applied. In this case, the polymer layer to be formed is to have a structure for defining the pre-tilt angle to the liquid crystal molecules even in the state that no voltage is applied thereafter.

In Embodiment 1, use of a compound formed by further bonding a hydrocarbon group with 12 carbon atoms or more to a compound formed by bonding two polymerizable groups to a cyclic aliphatic compound or an aromatic compound with 6 carbon atoms or more can keep high voltage holding ratio (VHR).

Other constituent elements of a liquid crystal display device of Embodiment 1 will be described in detail.

In the liquid crystal display device of Embodiment 1, the array substrate 110, the liquid crystal layer 105 and the color filter substrate 120 are layered in this order from the back side of the liquid crystal display device to the observation side. Polarizing plates are installed in the back side of the array substrate 110 and in the observation side of the color filter substrate 120. A retardation film may be arranged for these polarizing plates and the polarizing plates may be circular polarization plates.

The liquid crystal display device of Embodiment 1 may be a transmission type, a reflection type, and a transmission/reflection combined type. In the case of a transmission type or a transmission/reflection combined type, the liquid crystal display device of Embodiment 1 is further equipped with a back light unit. The back light unit is arranged in the further back side of the array substrate 110 and arranged in a manner that light is transmitted through the array substrate 110, the liquid crystal layer 105, and the color filter substrate 120 in this order. In the case of a reflection type or a transmission/reflection combined type, the array substrate 110 is equipped with a reflector for reflecting outside light. Further, in a region in which at least the reflected light is used for display, the polarizing plate of the color filter substrate 120 is required to have a circular polarization plate equipped with so-called λ/4 retardation film.

The liquid crystal layer 105 is filled with a liquid crystal material having a property of aligning in a specified direction by applying a certain voltage. The alignment property of the liquid crystal molecules in the liquid crystal layer 105 is controlled based on application of voltage not lower than the threshold value.

Regarding the liquid crystal display device of Embodiment 1, the liquid crystal display device (e.g. a mobile phone, a monitor, a liquid crystal TV (television), and information display) is disassembled and the monomer components existing in the polymer layer are analyzed by carrying out chemical analysis using NMR (nuclear magnetic resonance), FT-IR (Fourier transform infrared spectroscopy), MS (mass spectrometry), etc. and thus the types of the monomer components can be determined.

Embodiment 2

Embodiment 2 is same as Embodiment 1, except that a monomer having a structure for producing a radical by light irradiation is used in addition to the radical polymerizable monomer used in Embodiment 1.

Figure 3:
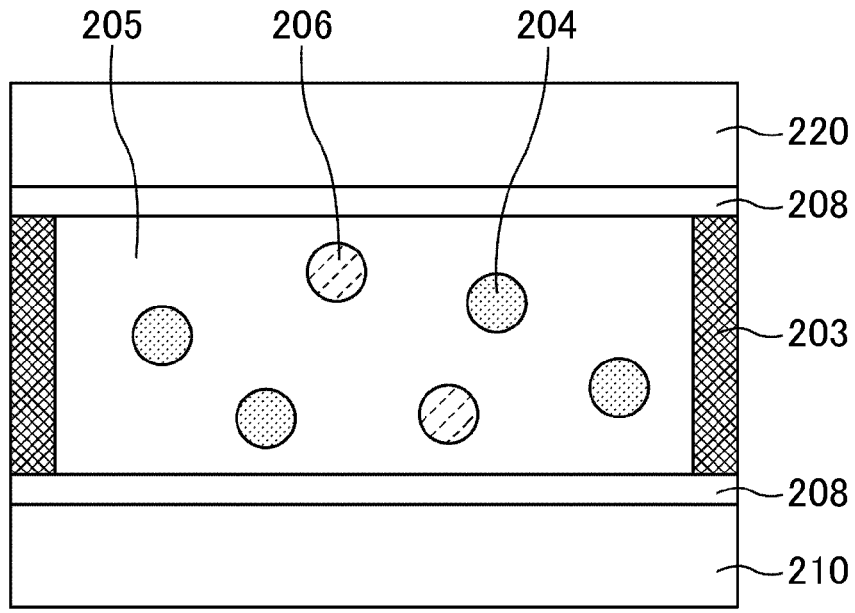
FIG. 3 is a schematic view of a cross section of a liquid crystal display device of Embodiment 2 before a PSA polymerization step.
Figure 4:
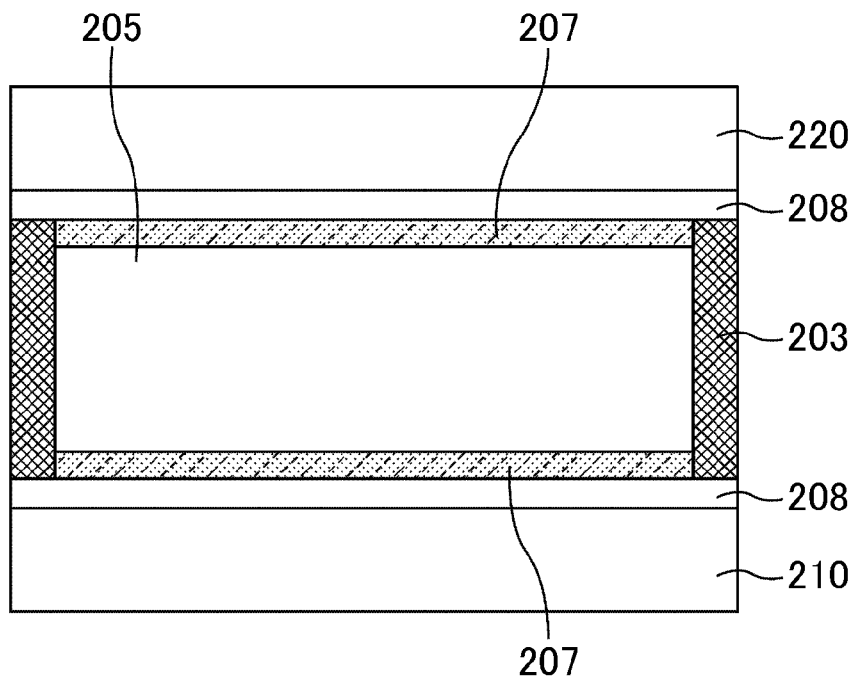
FIG. 4 is a schematic view of a cross section of a liquid crystal display device of Embodiment 2 after a PSA polymerization step.

Hereinafter, one example of a production method of a liquid crystal display device of Embodiment 2 will be described. FIG. 3 and FIG. 4 are schematic views of a cross section of a liquid crystal display device of Embodiment 2. FIG. 3 illustrates a view before the PSA polymerization step and FIG. 4 illustrates a view after the PSA polymerization step. As illustrated in FIG. 3 and FIG. 4, the liquid crystal display device of Embodiment 2 has an array substrate 210, a color filter substrate 220, and a liquid crystal layer 205 sandwiched between a pair of the substrates, that is, the array substrate 210 and the color filter substrate 220. The array substrate 210 has an insulating transparent substrate made of a material such as glass or the like, and various kinds of wiring, a pixel electrode, and a TFT (thin film transistor) formed on the transparent substrate. The color filter substrate 220 has an insulating transparent substrate made of a material such as glass or the like, and a color filter, a black matrix, and a common electrode formed on the transparent substrate. The array substrate 210 and the color filter substrate 220 are respectively provided with an alignment film 208 on the surfaces having contact with the liquid crystal layer 205 side.

As illustrated in FIG. 3, before the PSA polymerization step, the liquid crystal layer 205 contains a liquid crystal material, a first radical polymerizable monomer 204, and a second radical polymerizable monomer 206. The first radical polymerizable monomer 204 is a compound formed by further bonding a hydrocarbon group with 12 carbon atoms or more to a compound formed by bonding two polymerizable groups to a cyclic aliphatic compound or an aromatic compound with 6 carbon atoms or more. Practical examples of the first radical polymerizable monomer 204 are same as those of the radical polymerizable monomer 104 in Embodiment 1.

The second radical polymerizable monomer 206 is a monomer having a structure for producing a radical by light irradiation and may be a compound having a structure for producing a radical by hydrogen abstraction reaction by light irradiation and a compound having a structure for producing a radical by self-cleavage reaction by light irradiation. The compound having a structure for producing a radical by hydrogen abstraction reaction by light irradiation is practically a compound represented by the above-mentioned formula (4) and more practically a compound represented by one of the above-mentioned formulas (6-1) to (6-8). The compound having a structure for producing a radical by self-cleavage reaction by light irradiation is practically a compound represented by the above-mentioned formula (5) and more practically a compound represented by the above-mentioned formula (7).

Both of the first radical polymerizable monomer 204 and the second radical polymerizable monomer 206 independently produce radicals by irradiating the liquid crystal layer 205 with light and using the radicals as active species, the radical polymerizable groups of the first radical polymerizable monomer 204 and the second radical polymerizable monomer 206 successively start and promote chain polymerization to be polymerized. The polymer formed by the polymerization is deposited in the form of a polymer layer (PSA layer) 207 on the alignment film 208 formed on the substrates 210 and 220 as illustrated in FIG. 4.

As illustrated in FIG. 4, in Embodiment 2, the polymer layer 207 is formed on the surface of the alignment film 208 formed on the array substrate 210 and the color filter substrate 220. Between the array substrate 210 and the color filter substrate 220, a sealing material 203 is stuck to the alignment film 208 along the outer rim of these substrates 210 and 220 and the liquid crystal layer 205 is enclosed between the array substrate 210 and the color filter substrate 220 by the sealing material 203. Radiation of the liquid crystal layer 205 with light is carried out after sealing the liquid crystal layer 205 by the sealing material 203 so that the polymer layer 207 is formed in the region surrounded with the sealing material 203.

In Embodiment 2, use of a compound formed by further bonding a hydrocarbon group with 12 carbon atoms or more to a compound formed by bonding two polymerizable groups to a cyclic aliphatic compound or an aromatic compound with 6 carbon atoms or more and use of a monomer having a structure for producing a radical by light irradiation in combination can keep high voltage holding ratio (VHR) same as in Embodiment 1. The polymer layer by which vertical alignment of liquid crystal molecules can be induced can be formed so that liquid crystal molecules can be aligned vertically to the substrate face.

Embodiment 3

Embodiment 3 is same as Embodiment 1, except that a monomer having a structure for producing a radical by light irradiation is used in addition to the radical polymerizable monomer used in Embodiment 1 and the outermost faces of the array substrate and the color filter substrate are substantially not composed of an alignment film.

Figure 5:
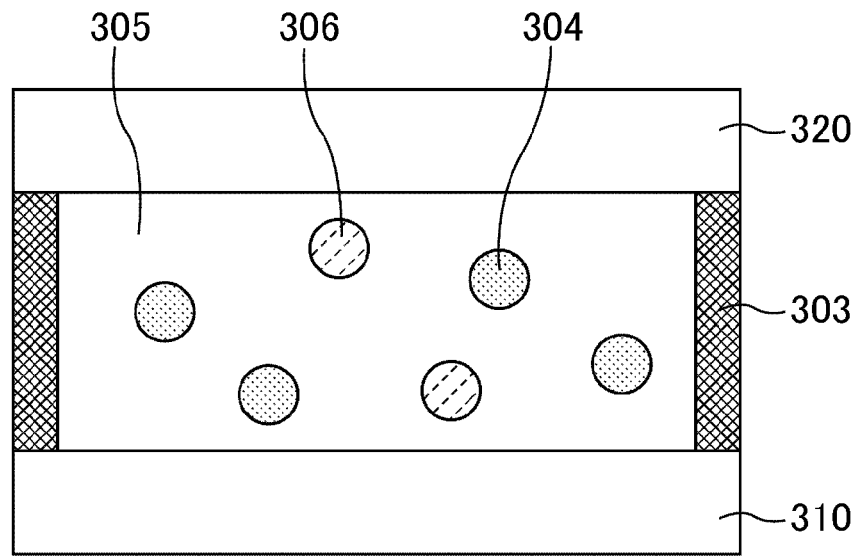
FIG. 5 is a schematic view of a cross section of a liquid crystal display device of Embodiment 3 before a PSA polymerization step.
Figure 6:
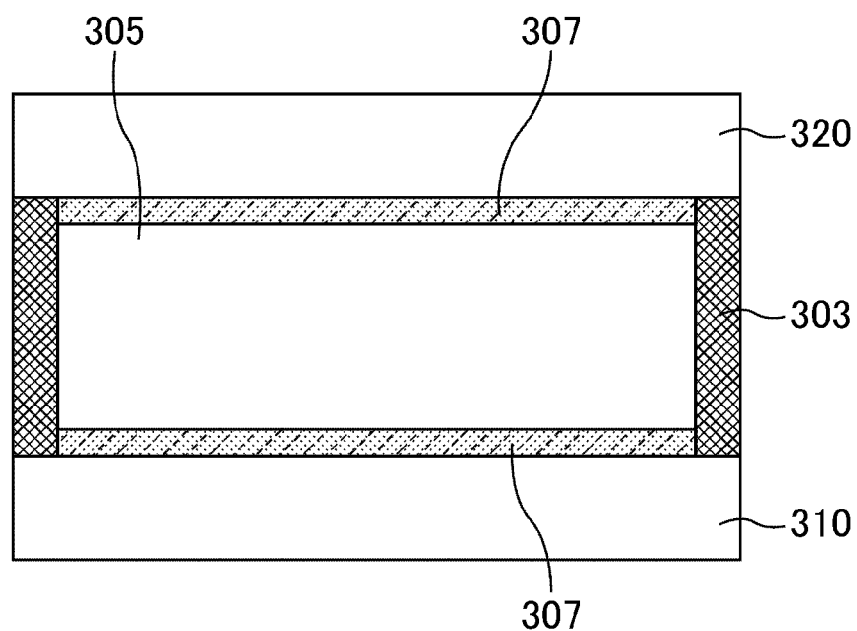
FIG. 6 is a schematic view of a cross section of a liquid crystal display device of Embodiment 3 after the PSA polymerization step.

Hereinafter, one example of a production method of a liquid crystal display device of Embodiment 3 will be described. FIG. 5 and FIG. 6 are schematic cross sectional views of a liquid crystal display device of Embodiment 3 and FIG. 5 illustrates the view before a PSA polymerization step and FIG. 6 illustrates the view after the PSA polymerization step. As illustrated in FIG. 5 and FIG. 6, the liquid crystal display device of Embodiment 3 has an array substrate 310, a color filter substrate 320, and a liquid crystal layer 305 sandwiched between a pair of the substrates, that is, the array substrate 310 and the color filter substrate 320. The array substrate 310 has an insulating transparent substrate made of a material such as glass or the like, and various kinds of wiring, a pixel electrode, and a TFT (thin film transistor) formed on the transparent substrate. The color filter substrate 320 has an insulating transparent substrate made of a material such as glass or the like, and a color filter, a black matrix, and a common electrode formed on the transparent substrate. The outermost faces of the array substrate 310 and the color filter substrate 320 are substantially not composed of an alignment film.

In this Embodiment, "alignment film" means a monolayer film or a multilayer film formed by using a polyimide, a polyamic acid, a polyamide, a polymaleimide, a polysiloxane, or a their copolymer, or a film formed by oblique vapor deposition of a silicon oxide and is a film capable of controlling alignment of liquid crystal molecules. In a common liquid crystal display device, an alignment film is formed by directly applying an alignment film material (e.g. applying a polyimide or the like) to or carrying out vapor deposition (e.g. oblique vapor deposition of silicon oxide (SiO) on a substrate face in a display region. The display region means a region for forming images which an observer recognizes and the region excludes, for example, a peripheral region of terminal parts or the like. The above-mentioned alignment film is not limited to those which are subjected to an alignment treatment and is an applied film made of an already existing alignment film material such as a polyimide or the like.

As illustrated in FIG. 5, before the PSA polymerization step, the liquid crystal layer 305 contains a liquid crystal material, a first radical polymerizable monomer 304, and a second radical polymerizable monomer 306. The first radical polymerizable monomer 304 is a compound formed by further bonding a hydrocarbon group with 12 carbon atoms or more to a compound formed by bonding two polymerizable groups to a cyclic aliphatic compound or an aromatic compound with 6 carbon atoms or more. Practical examples of the first radical polymerizable monomer 304 are same as those of the radical polymerizable monomer 104 in Embodiment 1. The second radical polymerizable monomer 306 is a monomer having a structure for producing a radical by light irradiation. The monomer 306 having the structure for producing a radical by light irradiation may be a compound having a structure for producing a radical by hydrogen abstraction reaction by light irradiation and a compound having a structure for producing a radical by self-cleavage reaction by light irradiation. Practical examples of the second radical polymerizable monomer 306 are same as those of the radical polymerizable monomer 206 in Embodiment 2.

Both of the first radical polymerizable monomer 304 and the second radical polymerizable monomer 306 produce radicals by radiating the liquid crystal layer 305 with light and using the radicals as active species, the radical polymerizable groups of the first radical polymerizable monomer 304 and the second radical polymerizable monomer 306 successively start and promote chain polymerization to be polymerized. The polymer formed by the polymerization is deposited in the form of a polymer layer (PSA layer) 307 on the substrates 310 and 320 as illustrated in FIG. 6.

As illustrated in FIG. 6, in Embodiment 3, the polymer layer (PSA layer) 307 is formed on the surface of the array substrate 310 and the color filter substrate 320 having no alignment film. Between the array substrate 310 and the color filter substrate 320, a sealing material 303 is stuck directly to the substrates 310 and 320 along the outer rim of these substrates 310 and 320 and the liquid crystal layer 305 is enclosed between the array substrate 310 and the color filter substrate 320 by the sealing material 303. Radiation of the liquid crystal layer 305 with light is carried out after sealing the liquid crystal layer 305 by the sealing material 303 so that the polymer layer 307 is formed in the region surrounded with the sealing material 303.

In Embodiment 3, even in the case where no alignment film is formed, use of a compound formed by further bonding a hydrocarbon group with 12 carbon atoms or more to a compound formed by bonding two polymerizable groups to a cyclic aliphatic compound or an aromatic compound with 6 carbon atoms or more and use of a monomer having a structure for producing a radical by light irradiation in combination can keep high voltage holding ratio (VHR). The polymer layer having high alignment controllability for liquid crystal molecules can be formed so that liquid crystal molecules can be aligned vertically to the substrate face.

Hereinafter, described are synthesis Examples for actually synthesizing a compound formed by further bonding a hydrocarbon group with 12 carbon atoms or more to a compound formed by bonding two polymerizable groups to a cyclic aliphatic compound or an aromatic compound with 6 carbon atoms or more.

Synthesis Example 1

In Synthesis Example 1, 3-hexadecanyl-4,4'-dimethacryloxybiphenyl was synthesized as a practical example of a compound represented by the above-mentioned formula (3-1).

At first, as illustrated in the following formula (8), 3.0 g of 4,4'-biphenol (compound A) was dissolved in 18 g of acetonitrile and mixed with potassium carbonate and stirred for 10 minutes. Thereafter, 0.57 g of dimethyl sulfate was added and the resulting solution was heated until the temperature became 60° C. Successively, the solution was stirred for 15 hours and filtered and pure water was dropwise added to the filtrate to precipitate crystals. The obtained crystals were recovered by filtration and dried to obtain 4,4'-dimethoxybiphenyl (compound B) at 90% yield.

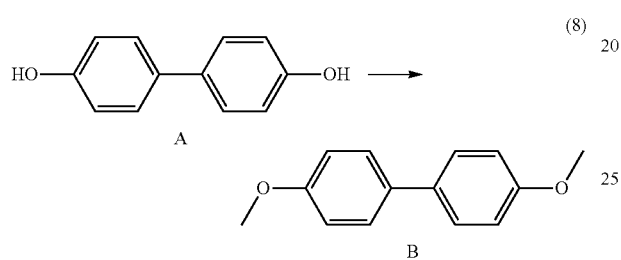

Next, as illustrated in the following formula (9), 3 g of compound B was dissolved in 90 g of methylene chloride and cooled until the solution temperature became 0° C. After 1.87 g of aluminum chloride was added to the resulting solution and stirred for 30 minutes, the solution was heated until the solution temperature became 25° C. and stirred further for 2 hours. Thereafter, the resulting solution was cooled until the temperature became 0° C. and mixed with 24 g of pure water. Successively, the organic layer was recovered and washed with pure water 3 times and further with saturated salt water and then the solvent was removed. Thereafter, the product was refined by silica gel column chromatography using an ethyl acetate/hexane (4/96) solution as an eluent to obtain 3-hexadecanyl-4,4'-dimethoxybiphenyl (compound C) at 63% yield.

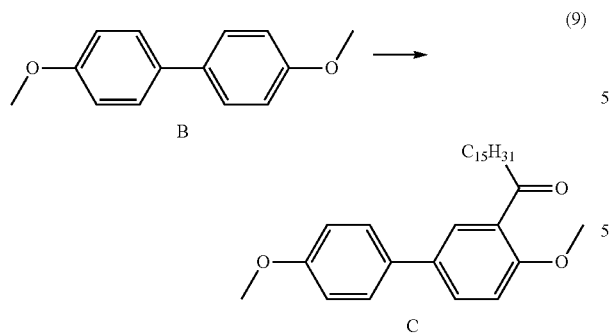

Next, as illustrated in the following formula (10), 3 g of compound C was dissolved in 60 g methylene chloride and mixed with 1.7 g of triethylsilane. A solution obtained by dissolving 7.5 g of trifluoroacetic acid in 15 g of methylene chloride was dropwise added to the above-mentioned resulting solution in 30 minutes. On completion of the dropwise addition, the resulting solution was stirred for 1 hour and cooled until the temperature became 10° C. After 58 g of an aqueous 5% sodium hydroxide solution was added thereto and the obtained solution mixture was separated, was washed 3 times and washed with saturated salt water and the obtained solution was separated. Thereafter, the solvent was removed therefrom to obtain 3-hexadecanyl-4,4'-dimethoxybiphenyl (compound D) at 86% yield.

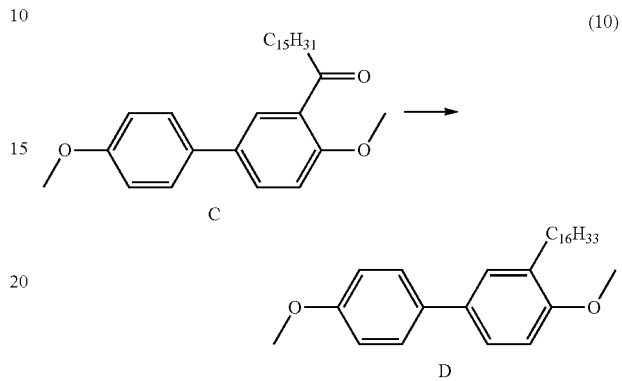

Next, as illustrated in the following formula (11), 2.8 g of a compound D was dissolved in 56 g of acetic acid and mixed with 10.8 g of an aqueous 48% HBr solution and thereafter heated until the solution temperature became 110° C. Successively, the solution was stirred for 15 hours, cooled, and mixed with 112 g of pure water to precipitate crystals. The crystals were recovered by filtration, sufficiently washed with pure water, re-dissolved in 56 g of ethyl acetate, and separated and washed with pure water 4 times. Thereafter, the solvent was removed therefrom to obtain 3-hexadecanyl-4,4'-dihydroxybiphenyl (compound E) at 86% yield.

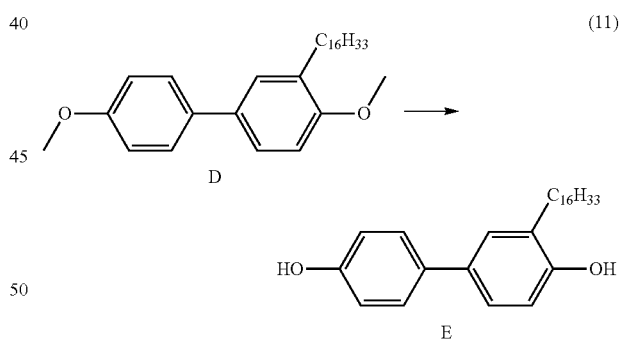

As illustrated in the following formula (12), 2.2 g of the compound E was dissolved in 22 g of tetrahydrofuran (THF) and 1.27 g of triethylamine (TEA) and 0.033 g of 4-dimethylaminopyridine (DMAP) were added to the obtained solution and stirred. After 1.90 g of methacrylic anhydride was dropwise added in 10 minutes to the obtained solution and stirred for 2 hours, 30 g of an aqueous 1% HCl solution was added and stirred further for 10 minutes. Thereafter, extraction was carried out with 55 g of toluene and the extract was washed with pure water 4 times. Thereafter, the oily component obtained by removing the solvent was refined by silica gel column chromatography using an ethyl acetate/hexane (2/98) solution as an eluent to obtain a compound F at 63% yield.

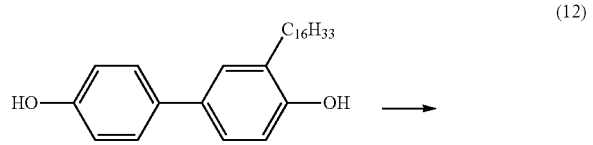

The analysis result of the obtained compound F by $^1$H-NMR (400 MHz) is as follows. $^1$H-NMR (CDCl$_3$, ppm): δ=0.88 (t, 3H, methyl group), 1.28 (m, 26H, methylene group), 1.58 (q, 2H, methylene group), 2.06 (s, 3H, methyl group), 2.10 (s, 3H, methyl group), 2.56 (t, 2H, methylene group), 5.78 (s, 2H, vinyl group), 6.38 (s, 2H, vinyl group), 7.13 (d, 1H, benzene ring), 7.18 (d, 2H, benzene ring), 7.41 (m, 2H, benzene ring), 7.57 (d, 2H, benzene ring)

According to the above-mentioned analysis result, the obtained compound F was proved to be the aimed compound, 3-hexadecanyl-4,4'-dimethacryloxybiphenyl.

Synthesis Example 2

In Synthesis Example 2, 3,5-dimethacryloxybenzoic acid n-dodecane ester was synthesized as a practical example of a compound represented by the above-mentioned formula (3-2).

At first, as illustrated in the following formula (13), 3.0 g of 3,5-dihydroxybenzoic acid (compound G) was dispersed in 24 g of anisole. The obtained dispersion, 8.8 g of n-dodecanol, and 0.57 g of sulfuric acid were loaded to a reactor equipped with a Dean-Stark tube and refluxed at 75° C. and 4 Torr for 8 hours. Thereafter, the reaction system was cooled and mixed with 1.2 g of triethylamine and stirred for 10 minutes. The precipitate was filtered and the residue was washed with 21 g of toluene and mixed with the filtrate and the solvent was removed. Thereafter, after an oily component was separated by adding 100 g of hexane, hexane was removed by decantation, the remaining oily component was mixed with 100 g of hexane, and the mixture was subjected to decantation further 2 times. The remaining oily component in a lower layer was vacuum-dried to obtain 5.4 g of a mixture of 3,5-dihydroxybenzoic acid n-dodecane ester (compound H) and dodecanol.

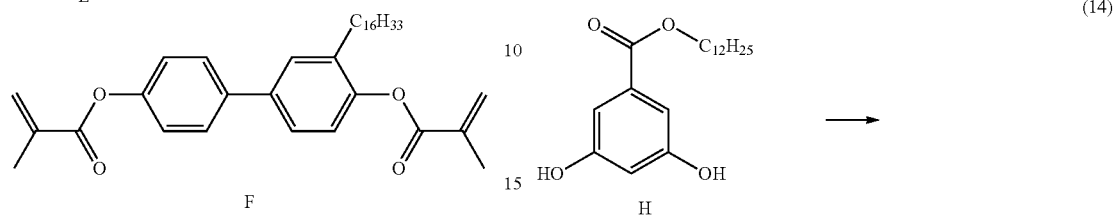

Next, as illustrated in the following formula (14), the mixture of the compound H and dodecanol was subjected to methacryl-esterification by the same reaction step as the above-mentioned formula (12). Thereafter, the obtained product was refined by silica gel column chromatography using an ethyl acetate/hexane (4/96) solution as an eluent to obtain a compound I at 57% yield.

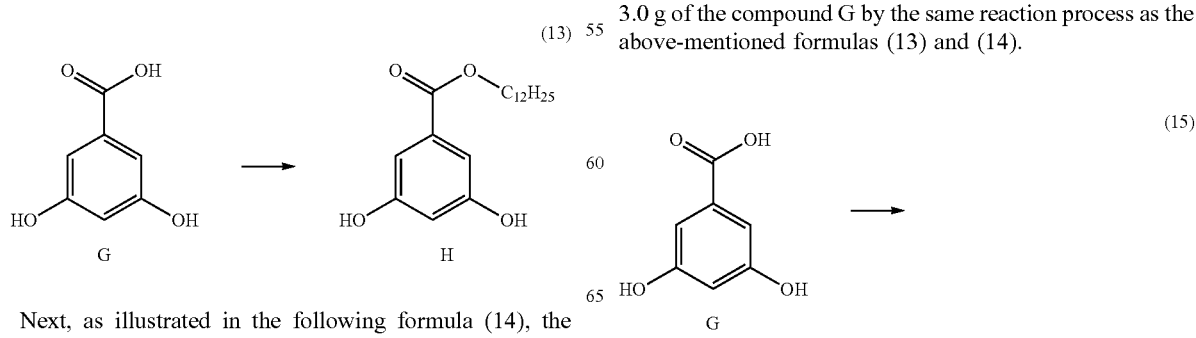

The analysis result of the obtained compound I by $^1$H-NMR (400 MHz) is as follows. $^1$H-NMR (CDCl$_3$, ppm): δ=0.89 (t, 3H, methyl group), 1.39 (m, 18H, methylene group), 1.75 (q, 2H, methylene group), 2.06 (s, 6H, methyl group), 4.31 (t, 2H, methylene group), 5.79 (s, 2H, vinyl group), 6.36 (s, 2H, vinyl group), 7.23 (s, 1H, benzene ring), 7.70 (s, 2H, benzene ring)

According to the above-mentioned analysis result, the obtained compound I was proved to be the aimed compound, 3,5-dimethacryloxybenzoic acid n-dodecane ester.

Synthesis Example 3

In Synthesis Example 3, 3,5-dimethacryloxybenzoic acid n-hexadecane ester was synthesized as a practical example of a compound represented by the above-mentioned formula (3-3).

Synthesis Example 3 was the same as represented by the above-mentioned formulas (13) and (14), except that n-dodecanol was replaced with n-hexadecanol. In Synthesis Example 3, as illustrated in the following chemical reaction formula (15), a compound J was obtained at 43% yield from 3.0 g of the compound G by the same reaction process as the above-mentioned formulas (13) and (14).

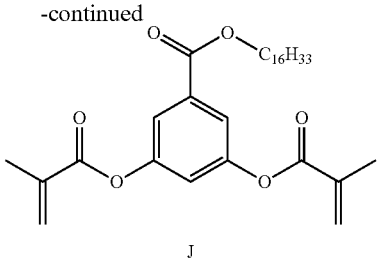

The analysis result of the obtained compound J by $^1$H-NMR (400 MHz) is as follows. $^1$H-NMR (CDCl$_3$, ppm): δ=0.88 (t, 3H, methyl group), 1.34 (m, 26H, methylene group), 1.75 (q, 2H, methylene group), 2.06 (s, 6H, methyl group), 4.31 (t, 2H, methylene group), 5.79 (s, 2H, vinyl group), 6.36 (s, 2H, vinyl group), 7.23 (s, 1H, benzene ring), 7.69 (s, 2H, benzene ring)

According to the above-mentioned analysis result, the obtained compound J was proved to be the aimed compound, 3,5-dimethacryloxybenzoic acid n-hexadecane ester.

Synthesis Example 4

In Synthesis Example 4, 3,5-dimethacryloxybenzoic acid cholesterol was synthesized as a practical example of a compound represented by the above-mentioned formula (3-4).

At first, as illustrated in the following formula (16), 8.00 g of methyl 3,5-dihydroxybenzoate (compound K) was dissolved in 56.0 g of THF. After 0.650 g of pyridinium p-toluenesulfonate (PPTS) was added to the obtained solution, the solution was heated until the solution temperature became 60° C. After 17.5 g of 3,4-dihydro-2H-pyran was dropwise added in 10 minutes to the solution and stirred for 15 hours and cooled until the solution temperature became 25° C., 0.52 g of TEA was added. Thereafter, a solution obtained by dissolving 1.04 g of NaOH in 8.0 g of pure water was added to the resulting solution and stirred, and the resulting solution was subjected to extraction by adding 160 g of cyclohexane, an organic layer was recovered therefrom by liquid separation and again the solution was extracted by adding 80 g of cyclohexane to the water layer. Those organic layers were mixed and the solvent was removed therefrom by distillation after washing with pure water 3 times to obtain methyl 3,5-di(tetrahydro-2H-pyran-2-yloxy)benzoate (compound L) at 64% yield.

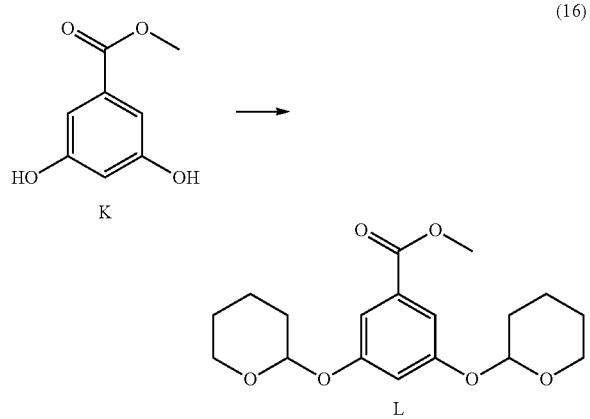

Next, as illustrated in the following formula (17), 11.0 g of the compound L was dissolved in 55.0 g of THF and heated until the solution temperature became 60° C. After 22.3 g of an aqueous 10% NaOH solution was dropwise added in 30 minutes to the obtained solution and stirred for 15 hours, the solution was cooled. THF was removed by distillation by using an evaporator and 55 g of pure water was added. Thereafter, 20 g of cyclohexane was added and stirred and resulting solution was subjected to decantation further 2 times. After that, a solution obtained by dissolving 4.6 g of an aqueous 35% HCl solution in 69 g of pure water was dropwise added to the water layer and the resulting solution was extracted with 110 g of ethyl acetate to separate and the organic layer obtained by liquid separation was washed with 88 g of pure water 2 times. Successively, the solvent was removed therefrom by distillation to obtain 3,5-di(tetrahydro-2H-pyran-2-yloxy)benzoic acid (compound M) at 53% yield.

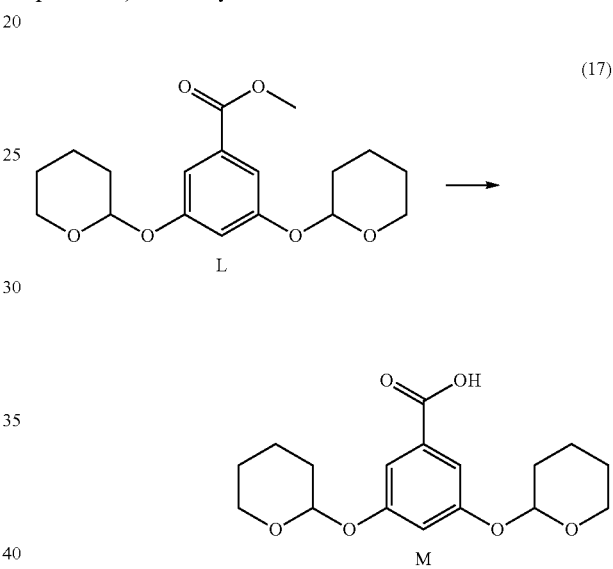

Next, as illustrated in the following formula (18), 1.3 g of the compound M was dissolved in 100 g of methylene chloride. Successively, 0.30 g of DMAP, 1.13 g of TEA and 3.07 g of cholesterol were added to the solution and dissolved. A solution obtained by dissolving 2.56 g of dicyclohexylcarbodiimide (DCC) in 12.8 g of methylene chloride was dropwise added to the resulting solution over 30 minutes. After stirred for 3 hours, the resulting solution was mixed with an 139 g of an aqueous 3% NaHCO$_3$ solution and stirred further for 10 minutes. After the precipitated solid was recovered by filtration and the resulting solution was subjected to liquid separation, the recovered methylene chloride layer was removed by distillation and the obtained residue was re-dissolved in 60 g of cyclohexane. The precipitated solid was recovered by filtration and the filtered substance was subjected to washing with pure water 3 times and thereafter the solvent was removed therefrom by distillation. After that, the product was refined by silica gel column chromatography using an ethyl acetate/hexane (3/100) solution as an eluent to obtain 3,5-di(tetrahydro-2H-pyran-2-yloxy)benzoic acid cholesterol (compound N) at 31% yield.

(18)

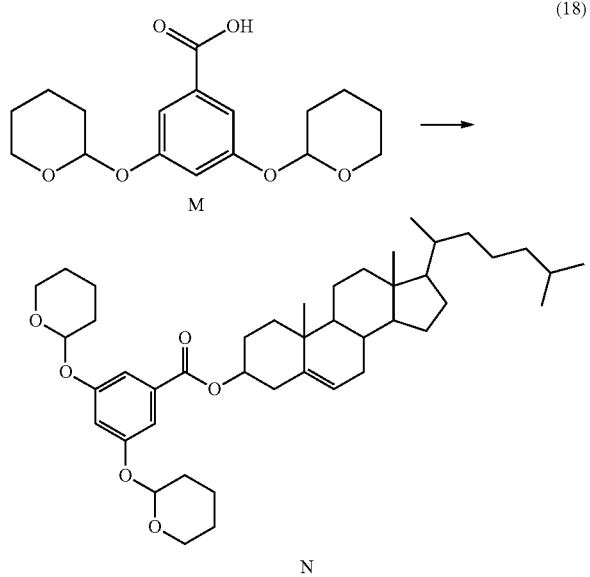

M

Next, as illustrated in the following formula (19), 2.5 g of the compound N was dissolved in 25 g of ethanol, 0.045 g of PPTS was added thereto, to heat until the solution temperature became 60° C. After stirred for 24 hours, the resulting solution was cooled until the temperature became 25° C. and 0.40 g of TEA was added. After the solvent was removed by distillation, acetonitrile was added thereto and the obtained crystals were recovered by filtration. The crystals were vacuum-dried to obtain 3,5-dihydroxybenzoic acid cholesterol (compound O) at 74% yield.

(19)

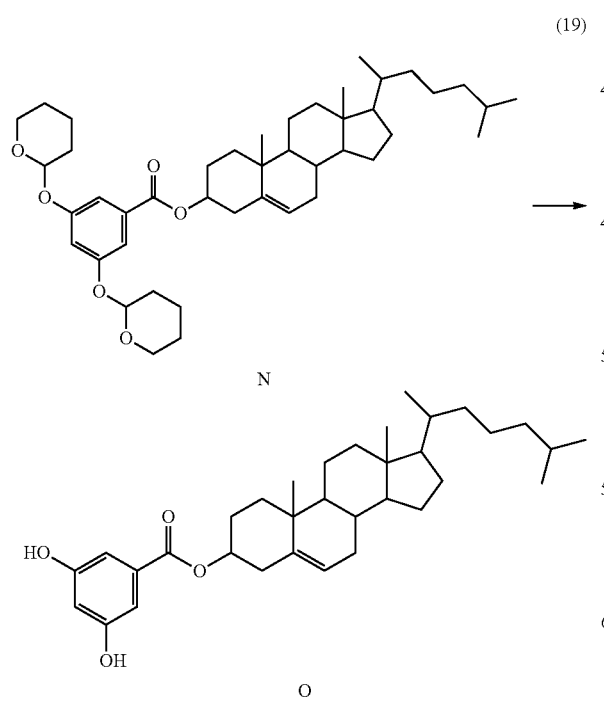

Next, as illustrated in the following formula (20), the compound O was methacryl-esterified by the same reaction step as the above-mentioned formula (12). Thereafter, the obtained product was refined by silica gel column chromatography using an ethyl acetate/cyclohexane (5/95) solution as an eluent to obtain a compound P at 41% yield.

(20)

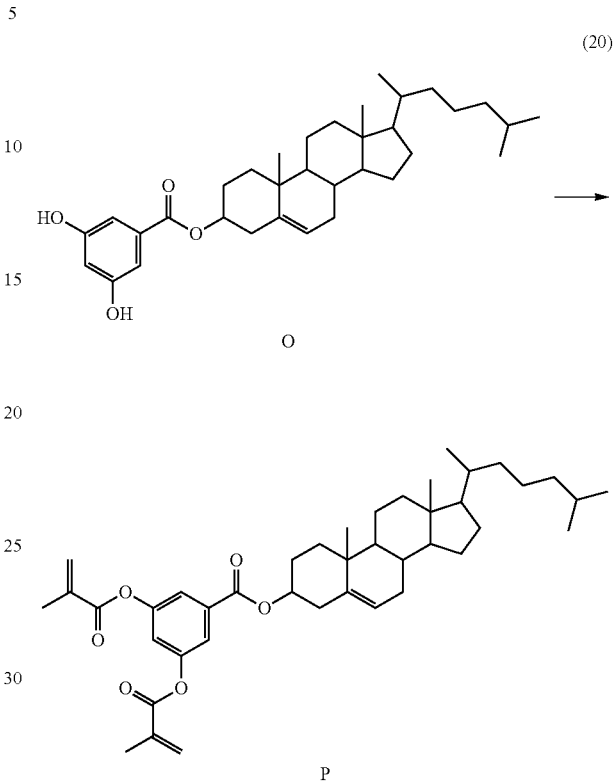

The analysis result of the obtained compound P by $^1$H-NMR (400 MHz) is as follows. $^1$H-NMR (CDCl$_3$, ppm): δ=0.74 (s, 3H, methyl group), 0.88 (d, 6H, methylene group), 0.97 (d, 3H, methylene group), 1.03-2.09 (m, 35H, methyl group), 2.46 (d, 2H, methylene group), 4.81 (m, 1H, methine group), 5.44 (m, 1H, methine group), 5.89 (s, 2H, vinyl group), 6.36 (s, 2H, vinyl group), 7.37 (s, 1H, benzene ring), 7.73 (s, 2H, benzene ring)

According to the above-mentioned analysis result, the obtained compound P was proved to be the aimed compound, 3,5-dimethacryloxybenzoic acid cholesterol.

Synthesis Example 5

In Synthesis Example 5, 3,5-dimethacryloxybenzoic acid (12-biphenyloxy)-dodecyl ester was synthesized as a practical example of a compound represented by the above-mentioned formula (3-5).

At first, 12-hydroxydodecyl biphenyl ether was obtained by using 1-bromododecanol as a raw material by the same reaction step as represented by the above-mentioned formula (8). Next, as illustrated in the following formula (21), the obtained 12-hydroxydodecyl biphenyl ether and 4-phenylphenol (compound Q) were tosylated using p-toluenesulfonic acid chloride by the same reaction step as represented by the above-mentioned formula (12) to obtain 12-p-toluenesulfonyloxy-dodecyl biphenyl ether (compound R) at 51% yield. Is in the following compound R denotes toluenesulfonyl group.

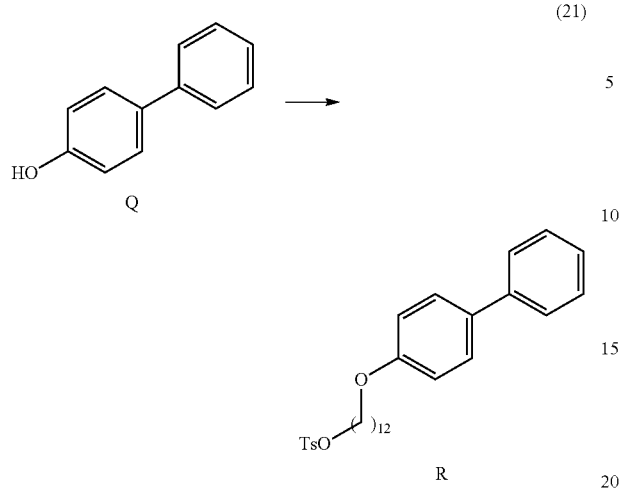

Next, as illustrated in the following formula (22), 2.0 g of the compound M obtained according to the above-mentioned formula (17) was dissolved in 20 g of DMF and 0.75 g of TEA was added thereto. After stirred for 10 minutes, the resulting solution was mixed with the compound R obtained according to the above-mentioned formula (21) and heated until the temperature became 70° C. After stirred for 15 hours, the resulting solution was cooled until the temperature became 25° C. and 80 g of pure water was added. Thereafter, the resulting solution was subjected to extraction with 30 g of toluene and the extract was washed with 15 g of pure water 3 times. Successively, toluene was removed therefrom by distillation to obtain 3,5-di(tetrahydro-2H-pyran-2-yloxy)benzoic acid (12-biphenyloxy)-dodecyl ester (compound S) at 60% yield.

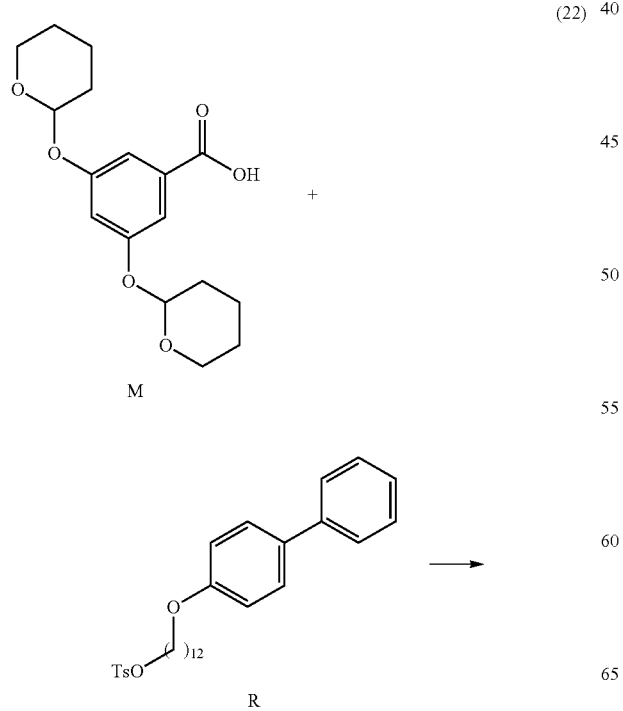

Next, as illustrated in the following formula (23), 2.45 g of the compound S was subjected to deprotection reaction by the same reaction step as represented by the above-mentioned formula (19) to quantitatively obtain 3,5-dihydroxy-benzoic acid (12-biphenyloxy)-dodecyl ester (compound T).

Next, as illustrated in the following formula (24), the compound T was methacryl-esterified by the same reaction step as the above-mentioned formula (12). Thereafter, the obtained product was refined by silica gel column chromatography using an ethyl acetate/cyclohexane (3/97) solution as an eluent to obtain a compound U at 58% yield.

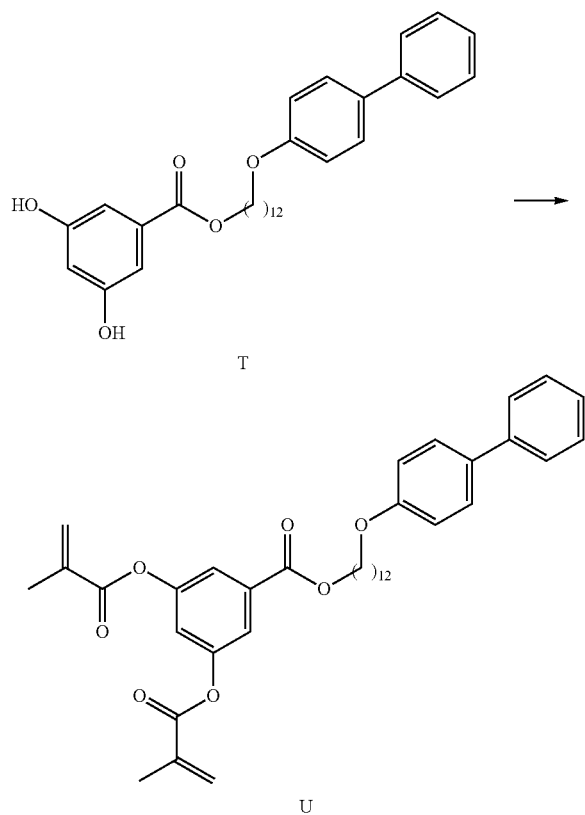

The analysis result of the obtained compound U by $^1$H-NMR (400 MHz) is as follows. $^1$H-NMR (CDCl$_3$, ppm): δ=1.40 (m, 16H, methylene group), 1.78 (m, 4H, methylene group), 2.06 (s, 6H, methyl group), 3.99 (t, 2H, methylene group), 4.31 (t, 2H, methylene group), 5.79 (s, 2H, vinyl group), 6.36 (s, 2H, vinyl group), 6.98 (d, 2H, benzene ring), 7.22 (s, 1H, benzene ring), 7.29 (t, 1H, benzene ring), 7.41 (t, 2H, benzene ring), 7.51 (d, 2H, benzene ring), 7.55 (d, 2H, benzene ring), 7.69 (s, 2H, benzene ring).

According to the above-mentioned analysis result, the obtained compound U was proved to be the aimed compound, 3,5-dimethacryloxybenzoic acid (12-biphenyloxy)-dodecyl ester.

Example 1

Hereinafter, a liquid crystal cell of Example 1 practically produced according to Embodiment 1 will be described.

In the case where the initial alignment of liquid crystal molecules is orthogonal to a substrate face, a vertical alignment film is used preferably. An alignment film material to be used for a vertical alignment film may include those obtained by introducing a side chain showing a vertical alignment property into a polyamic acid and carrying out imidization. But such an alignment film material is poor in wettability and tends to be uneven when applied to a substrate and thus causes unevenness of alignment of liquid crystal molecules. As a method for improving the wettability of an alignment film material, an alignment film formed by using an alignment film material with a horizontally aligning property was used in Example 1.

At first, a pair of substrates respectively having a transparent electrode on the surface were prepared and after the substrates were washed, an alignment film material having no vertically aligning property was applied to both substrates to form an alignment film. For example, a polyimide alignment film material showing a horizontally aligning property was used as the above-mentioned alignment film material. Use of such an alignment film material made it possible to form a uniform alignment film without coating unevenness. After the alignment film formation, the alignment film was pre-baked at 80° C. for 5 minutes and successively post-baked at 200° C. for 60 minutes.

Thereafter, a sealing material was applied to one substrate and then a liquid crystal composition containing a liquid crystal material having negative anisotropy of dielectric constant and a radical polymerizable monomer was dropped thereon, and subsequently, beads were sprayed as spacers to a counter substrate and the substrates were stuck to each other.

The liquid crystal cell produced in Example 1 was the following Sample A. For Sample A, the compound represented by the following formula (25) was added as a radical polymerizable monomer in an amount of 0.3 weight % in the entire liquid crystal composition. The compound represented by the following formula (25) was a compound F obtained in the above-mentioned Synthesis Example 1.

The liquid crystal cell produced in Comparative Example 1 was the following Sample B. For Sample B, a compound represented by the following formula (26) was added as a radical polymerizable monomer in an amount of 0.3 weight % in the entire liquid crystal composition.

In the state that no voltage was applied, Samples A and B were radiated with non-polarized ultraviolet rays (2.57 mW/cm$^2$) from a normal direction to the substrates for 30 minutes to polymerize the radical polymerizable monomers and thus liquid crystal cells were completed. A black light FHF-32BLB (wavelength region: 300 to 370 nm) manufactured by TOSHIBA Lighting & Technology Corporation was used as a light source for the non-polarized ultraviolet rays.

Regarding the completed respective liquid crystal cells, the alignment property of liquid crystal molecules was observed and initial voltage holding ratio (VHR) and voltage holding ratio (VHR) after an aging test were measured for the respective liquid crystal cells. The aging test was carried out by radiating each liquid crystal cell with backlight unit of a cold cathode fluorescent lamp for 1000 hours from the normal direction to the substrates.

The voltage holding ratio (VHR) was measured by using a 6254 model liquid crystal physical property measurement system manufactured by TOYO Corporation. After each liquid crystal cell was put in an oven at 70° C. and pulsed voltage was applied, potential between electrodes was measured for 16.6 ms open period (period for applying no voltage).

The following Table 1 represents the measurement results of the alignment property of liquid crystal molecules, the initial voltage holding ratio (initial VHR), and voltage holding ratio (VHR) after the aging test for Samples A and B.

TABLE 1

| | | Concentration of monomer in entire liquid crystal composition | Alignment property | Initial VHR (%) | VHR (%) after aging test |
|---|---|---|---|---|---|
| Example 1 | Sample A | Formula (25): 0.3(weight %) | Vertical alignment | 99.2 | 98.8 |
| Comparative Example 1 | Sample B | Formula (26): 0.3(weight %) | Horizontal alignment | 99.1 | 98.6 |

In Sample A, an example in an aspect of the present invention, the liquid crystal molecules were aligned vertically to the substrate face. The initial voltage holding ratio (VHR) was as high as 99% or higher and voltage holding ratio (VHR) was scarcely decreased even after the aging test. On the other hand, in Sample B, Comparative Example, the initial voltage holding ratio (initial VHR) and the voltage holding ratio (VHR) after the aging test were both high but the liquid crystal molecules were not aligned vertically to the substrate face.

Based on investigations on the above-mentioned results, it is supposed that since the compound of Sample A represented by the formula (25) has a hydrocarbon group with 12 carbon atoms or more, liquid crystal molecules are aligned by strong intermolecular interaction with the hydrocarbon group and aligned vertically to the substrate face.

On the other hand, since the compound of Sample B represented by the formula (26) does not have the hydrocarbon group included in the compound represented by the formula (25) has, intermolecular interaction with liquid crystal molecules is weak and the liquid crystal molecules cannot be aligned vertically to the substrate face.

As described above, even in the case where a horizontal alignment film was used, use of a compound formed by further bonding a hydrocarbon group with 12 carbon atoms or more to a compound formed by bonding two polymerizable groups to a cyclic aliphatic compound or an aromatic compound with 6 carbon atoms or more and represented by the above-mentioned formula (25) could align liquid crystal molecules vertically to the substrate face by strong intermolecular interaction with the liquid crystal molecules. Further, with no need of a polymerization initiator, a polymer layer capable of controlling the alignment of liquid crystal molecules could be formed. Still further, it was made possible to keep a high voltage holding ratio and to obtain a highly reliable liquid crystal display device.

Example 2

Hereinafter, a liquid crystal cell of Example 2 practically produced according to Embodiment 2 will be described. The production method for a liquid crystal cell employed in Example 2 was the same as that employed in Example 1, except that a vertically aligned film was formed using an alignment film material with a low imidization ratio and the time for light irradiation to polymerize the radical polymerizable monomer was changed to be 20 minutes.

As a method for improving the wettability of the alignment film material, a polyimide alignment film material with imidization ratio of 50% or lower for polyamic acid was used as the alignment film material for the vertical alignment film in Example 2. Use of such an alignment film material made it possible to form a uniform alignment film without coating unevenness.

Liquid crystal cells produced in Example 2 were the following Samples C to F. As a radical polymerizable monomer, a compound represented by the following formula (27) was added in an amount of 1.0 weight % for Sample C: a compound represented by the following formula (28) was added in an amount of 1.0 weight % for Sample D: a compound represented by the following formula (29) was added in an amount of 1.0 weight % for Sample E: and a compound represented by the following formula (30) was added in an amount of 1.0 weight % for Sample F in the entire liquid crystal compositions, respectively. The compound represented by the following formula (27) was the compound I obtained in the above-mentioned Synthesis Example 2: the compound represented by the following formula (28) was the compound J obtained in the above-mentioned Synthesis Example 3: the compound represented by the following formula (29) was the compound P obtained in the above-mentioned Synthesis Example 4: and the compound represented by the following formula (30) was the compound U obtained in the above-mentioned Synthesis Example 5.

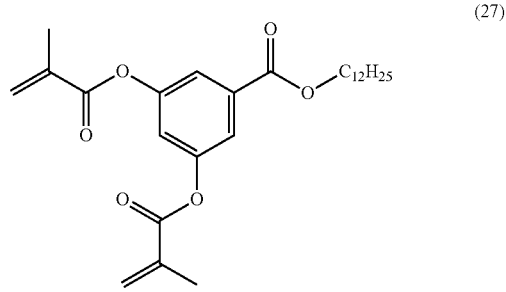

(27)

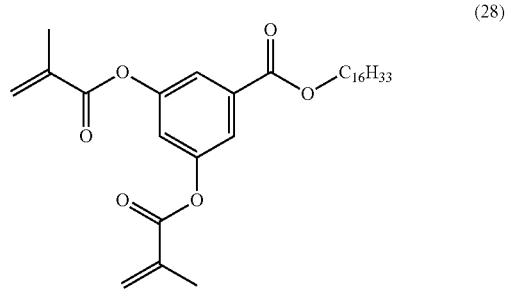

(28)

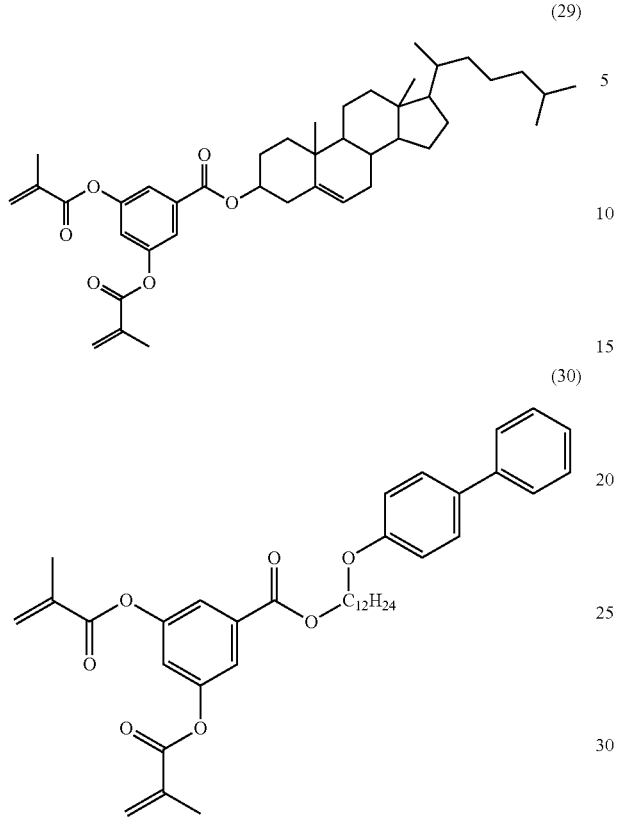

(29)

(30)

Further, for Samples C to F, a compound represented by the following formula (33) was added as a monomer having a structure for producing a radical by light irradiation in an amount of 0.05 weight % in the entire liquid crystal composition. The compound represented by the following formula (33) was a compound having a structure for producing a radical by hydrogen abstraction reaction by light irradiation.

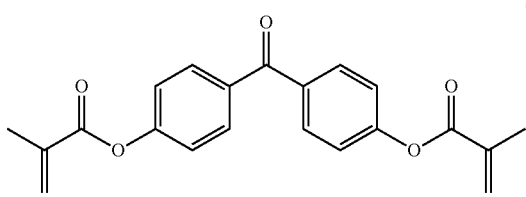

(33)

Liquid crystal cells produced in Comparative Example 2 were the following Samples G to I. In Sample G, no radical polymerizable monomer was added to the liquid crystal composition. A compound (dodecyl methacrylate) represented by the following formula (31) was added in an amount of 1.0 weight % for Sample H: and a compound represented by the following formula (32) was added in an amount of 1.0 weight % for Sample I in the entire liquid crystal compositions, respectively. Further, for Samples H and I, a compound represented by the above-mentioned formula (33) was added in an amount of 0.05 weight % in the entire liquid crystal composition.

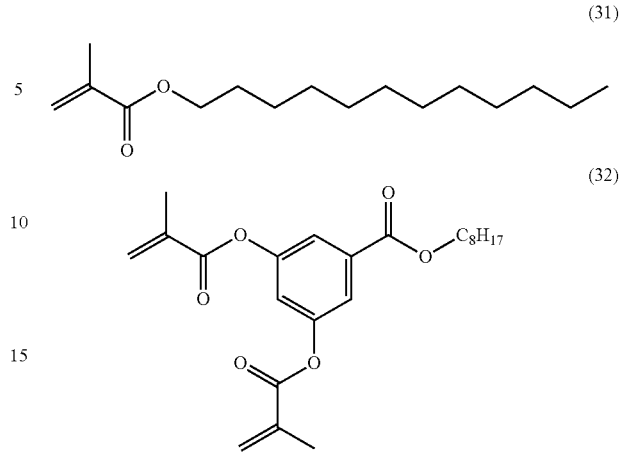

(31)

(32)

Regarding the completed respective liquid crystal cells, the alignment property of liquid crystal molecules was observed and initial voltage holding ratio (VHR) and voltage holding ratio (VHR) after an aging test were measured for the respective liquid crystal cells. The measurement method for voltage holding ratio (VHR) and the method for aging test were same as those in Example 1.

The following Table 2 represents the measurement results of the alignment property of liquid crystal molecules, the initial voltage holding ratio (initial VHR), and voltage holding ratio (VHR) after the aging test for Samples C to I.

TABLE 2

| | | Concentration of monomer in entire liquid crystal composition | Alignment property | Initial VHR (%) | VHR (%) after aging test |
|---|---|---|---|---|---|
| Example 2 | Sample C | Formula (27): 1.0 (weight %) + Formula (33): 0.05 (weight %) | Vertical alignment | 99.1 | 98.8 |
| | Sample D | Formula (28): 1.0 (weight %) + Formula (33): 0.05 (weight %) | Vertical alignment | 99.2 | 99.0 |
| | Sample E | Formula (29): 1.0 (weight %) + Formula (33): 0.05 (weight %) | Vertical alignment | 99.1 | 98.9 |
| | Sample F | Formula (30): 1.0 (weight %) + Formula (33): 0.05 (weight %) | Vertical alignment | 99.2 | 98.8 |
| Comparative Example 2 | Sample G | No monomer addition (no polymer layer) | Horizontal alignment | 98.1 | 94.0 |
| | Sample H | Formula (31): 1.0 (weight %) + Formula (33): 0.05 (weight %) | Vertical alignment | 98.0 | 90.5 |
| | Sample I | Formula (32): 1.0 (weight %) + Formula (33): 0.05 (weight %) | Horizontal alignment | 99.0 | 98.7 |

In Samples C to F, Examples in an aspect of the present invention, the liquid crystal molecules were aligned vertically to the substrate face in all Samples. In all of Samples C to F, the initial voltage holding ratio (initial VHR) was as high as 99% or higher and the voltage holding ratio (VHR) after the aging test was scarcely lowered.

Regarding Samples G to I, Comparative Examples, in Sample G and H, the initial voltage holding ratio (initial VHR) was about 98%, and slightly low, and the voltage holding ratio (VHR) after the aging test was so significantly lowered. In Sample I, the initial voltage holding ratio (initial VHR) was as high as 99% and the voltage holding ratio (VHR) after the aging test was scarcely lowered, but the liquid crystal molecules were not aligned vertically to the substrate face.

The above-mentioned results were comprehensively concluded as follows. Since no radical polymerizable monomer was added in Sample G, no polymer layer (PSA layer) was formed on the alignment film. Therefore, it was supposed that the carboxylic acid in the polyamic acid of the alignment film absorbed light from backlight unit and as a result, deterioration was promoted to result in decrease of the voltage holding ratio (VHR) after the aging test.

Since the compound represented by the above-mentioned formula (31) used for Sample H had one polymerizable group, the polymerization speed was so slow and the polymer was so hard to be taken in the polymer layer so that the radical generated in the polymerizable group at a polymerization terminal might remain in the liquid crystal layer and accordingly, it was supposed that the initial voltage holding ratio (initial VHR) was rather slightly lowered.

Since the compound represented by the above-mentioned formula (32) used for Sample I had two polymerizable groups, the reaction speed was high and the polymer layer was formed on the alignment film within a short time so that it was supposed that the initial voltage holding ratio (initial VHR) was high. Further, it was supposed that the voltage holding ratio (VHR) after the aging test was not lowered owing to the formation of the polymer layer. However, since the compound represented by the formula (32) has the hydrocarbon group with carbon atoms as low as 8, it is supposed that intermolecular interaction with liquid crystal molecules is weak and the liquid crystal molecules cannot sufficiently be aligned vertically to the substrate face.

As described above, even in the case where a vertical alignment film formed from the alignment film material with imidization ratio of 50% or lower was used, use of the compounds formed by further bonding a hydrocarbon group with 12 carbon atoms or more to a compound formed by bonding two polymerizable groups to a cyclic aliphatic compound or an aromatic compound with 6 carbon atoms or more and represented by the above-mentioned formulas (27) to (30) made it possible to form a polymer layer capable of controlling the alignment of the liquid crystal molecules. Further, use of a monomer represented by the above-mentioned formula (33) and having a structure for producing a radical by light irradiation in combination therewith made it possible to form the polymer layer with high alignment controllability for the liquid crystal molecules and to vertically align the liquid crystal molecules to the substrate face. Still further, it was made possible to keep a high voltage holding ratio and to obtain a highly reliable liquid crystal display device.

Example 3

Hereinafter, a liquid crystal cell of Example 3 practically produced according to Embodiment 3 will be described. The production method for a liquid crystal cell employed in Example 3 was same as that employed in Example 1, except that the method did not have a step for forming an alignment film on the surface of a substrate of the liquid crystal cell and that the time for light irradiation to polymerize the radical polymerizable monomer was changed to be 20 minutes.

Liquid crystal cells produced in Example 3 were the following Samples J to M. For Samples J to M, compounds represented by the above-mentioned formulas (27) to (30) were added as a radical polymerizable monomer in an amount of 1.0 weight % in the entire liquid crystal compositions, respectively, as same in Example 2. Further, for Samples J to M, a compound represented by the following formula (34) was added as a monomer having a structure for producing a radical by light irradiation in an amount of 0.05 weight % in the entire liquid crystal composition. The compound represented by the following formula (34) was a compound having a structure for producing a radical by self-cleavage reaction by light irradiation.

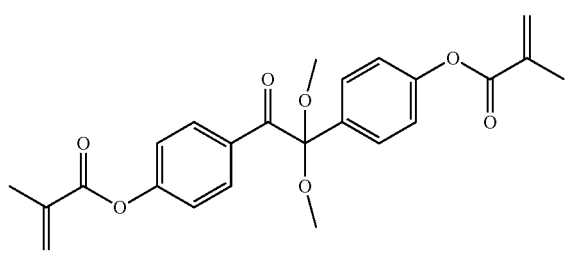

(34)

Liquid crystal cells produced in Comparative Example 3 were the following Samples N to P. In Sample N, no radical polymerizable monomer was added to the liquid crystal composition. A compound represented by the above-mentioned formula (31) was added in an amount of 1.0 weight % for Sample O: and a compound represented by the above-mentioned formula (32) was added in an amount of 1.0 weight % for Sample P in the entire liquid crystal compositions, respectively. Further, for Samples O and P, a compound represented by the above-mentioned formula (34) was added in an amount of 0.05 weight % in the entire liquid crystal composition.

Regarding the completed respective liquid crystal cells, the alignment property of liquid crystal molecules was observed and initial voltage holding ratio (VHR) and voltage holding ratio (VHR) after an aging test were measured for the respective liquid crystal cells. The measurement method for voltage holding ratio (VHR) and the method for aging test were same as those in Example 1.

The following Table 3 represents the measurement results of the alignment property of liquid crystal molecules, the initial voltage holding ratio (initial VHR), and voltage holding ratio (VHR) after the aging test for Samples J to P.

TABLE 3

| | | Concentration of monomer in entire liquid crystal composition | Alignment property | Initial VHR (%) | VHR (%) after aging test |
|---|---|---|---|---|---|
| Example 3 | Sample J | Formula (27): 1.0 (weight %) + Formula (34): 0.05 (weight %) | Vertical alignment | 99.4 | 99.5 |
| | Sample K | Formula (28): 1.0 (weight %) + Formula (34): 0.05 (weight %) | Vertical alignment | 99.4 | 99.5 |

TABLE 3-continued

| | | Concentration of monomer in entire liquid crystal composition | Alignment property | Initial VHR (%) | VHR (%) after aging test |
|---|---|---|---|---|---|
| | Sample L | Formula (29): 1.0 (weight %) + Formula (34): 0.05 (weight %) | Vertical alignment | 99.5 | 99.5 |
| | Sample M | Formula (30): 1.0 (weight %) + Formula (34): 0.05 (weight %) | Vertical alignment | 99.5 | 99.5 |
| Comparative Example 3 | Sample N | No monomer addition (no polymer layer) | Horizontal alignment | 99.4 | 97.2 |
| | Sample O | Formula (31): 1.0 (weight %) + Formula (34): 0.05 (weight %) | Vertical alignment | 98.5 | 92.3 |
| | Sample P | Formula (32): 1.0 (weight %) + Formula (34): 0.05 (weight %) | Horizontal alignment | 99.5 | 99.4 |

In Samples J to M, Examples in an aspect of the present invention, the liquid crystal molecules were aligned vertically to the substrate face in all Samples. In all of Samples J to M, the initial voltage holding ratio (initial VHR) was as high as 99% or higher and the voltage holding ratio (VHR) after the aging test was scarcely lowered.

Regarding Samples N to P, Comparative Example, in Sample N, the liquid crystal molecules were not vertically aligned to the substrate face and although the initial voltage holding ratio (initial VHR) was high, the voltage holding ratio (VHR) after the aging test was lowered to 97% level. In Sample O, although the liquid crystal molecules were vertically aligned to the substrate face, the initial voltage holding ratio (initial VHR) was slightly low and the voltage holding ratio (VHR) after the aging test was lowered to 92% level. In Sample P, both of the initial voltage holding ratio (VHR) and the voltage holding ratio (VHR) after the aging test showed high values but the liquid crystal molecules were not aligned vertically to the substrate face.

The above-mentioned results were comprehensively concluded as follows. In Sample N, no polymer layer was formed so that the liquid crystal molecules could not be aligned vertically to the substrate face. Since having only one polymerizable group, the compound represented by the above-mentioned formula (31) used for Sample O remained in the liquid crystal layer and thus it was supposed that the voltage holding ratio (VHR) after the aging test was considerably lowered. The compound represented by the formula (32) used for Sample P had the hydrocarbon group with small carbon atoms and it was supposed that intermolecular interaction with liquid crystal molecules was weak and the liquid crystal molecules could not sufficiently be aligned vertically to the substrate face.

As described above, even in the case where no alignment film was formed, use of compounds represented by the above-mentioned formulas (27) to (30) and formed by further bonding a hydrocarbon group with 12 carbon atoms or more to a compound formed by bonding two polymerizable groups to a cyclic aliphatic compound or an aromatic compound with 6 carbon atoms or more and use of a monomer represented by the above-mentioned formula (34) and having a structure for producing a radical by light irradiation in combination made it possible to form a polymer layer with high alignment controllability for liquid crystal molecules and to align liquid crystal molecules vertically to the substrate face. Still further, in the same manner as that in Example 2, it was made possible to keep a high voltage holding ratio and to obtain a highly reliable liquid crystal display device.

REFERENCE SIGNS LIST

| | |
|---|---|
| 103, 203, 303 | Sealing material |
| 104, 204, 304 | (First) radical polymerizable monomer |
| 105, 205, 305 | Liquid crystal layer |
| 206, 306 | (Second) radical polymerizable monomer |
| 107, 207, 307 | Polymer layer (PSA layer) |
| 108, 208 | Alignment film |
| 110, 210, 310 | Array substrate |
| 120, 220, 320 | Color filter substrate |

The invention claimed is:

1. A liquid crystal composition comprising a liquid crystal material and one or more kinds of monomers,
the one or more monomers including:
a first monomer produced by further bonding a hydrocarbon group with 12 carbon atoms or more to a compound produced by bonding two polymerizable groups to a cyclic aliphatic compound or aromatic compound with 6 carbon atoms or more; and
a second monomer having a structure for producing a radical by light irradiation; wherein
the first monomer produced by further bonding a hydrocarbon group with 12 carbon atoms or more to a compound produced by bonding two polymerizable groups to the cyclic aliphatic compound or aromatic compound with 6 carbon atoms or more is a compound represented by the following formula (2):

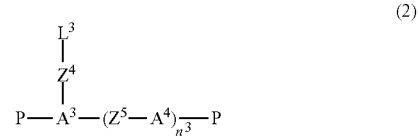

in the formula,
P and P are the same or different, and denote a (meth)acryloyloxy, (meth)acryloylamino, vinyl, or vinyloxy group;
$A^3$ denotes a trivalent, alicyclic, aromatic monocyclic, or condensed polycyclic hydrocarbon group;
the trivalent, alicyclic, aromatic monocyclic, or condensed polycyclic hydrocarbon group is selected from the group consisting of benzene-1,2,3-triyl, benzene-1,2,4-triyl, benzene-1,3,5-triyl, pyridine-2,3,4-triyl, pyridine-2,3,5-triyl, pyridine-2,4,6-triyl, naphthalene-1,2,5-triyl, naphthalene-1,2,6-triyl, naphthalene-1,2,7-triyl, naphthalene-1,2,8-triyl, naphthalene-1,3,5-triyl, naphthalene-1,3,6-triyl, naphthalene-1,3,7-triyl, naphthalene-1,3,8-triyl, naphthalene-1,4,5-triyl, naphthalene-1,4,6-triyl, naphthalene-1,4,7-triyl, naphthalene-1,6,7-triyl, naphthalene-1,6,8-triyl, naphthalene-2,3,6-triyl, cyclohexane-1,2,3-triyl, cyclohexane-1,2,4-triyl, cyclohexane-1,3,5-triyl, decahydronaphthalene-1,2,5-triyl, decahydronaphthalene-1,2,6-triyl, decahydronaphthalene-1,2,7-triyl, decahydronaphthalene-1,2,8-triyl, decahydronaphthalene-1,3,5-triyl, decahydronaphthalene-1,3,6-triyl, decahydronaphthalene-1,3,7-triyl, decahydronaphthalene-1,3,8-triyl, decahydronaphthalene-1,4,5-triyl, decahydronaphthalene-1,4,6-triyl, decahydronaphthalene-1,4,7-triyl, decahydronaphthalene-1,6,7-triyl, decahydronaphthalene-1,6,8-triyl, decahydronaphthalene-2,3,6-triyl, indan-1,1,5-triyl, indan-1,1,6-triyl, indan-1,3,5-triyl, indan-1,3,6-triyl, phenanthrene-1,2,6-triyl, phenanthrene-1,2,7-triyl, phenanthrene-1,2,8-triyl, phenanthrene-1,2,9-triyl, phenanthrene-1,3,6-triyl, phenanthrene-1,3,7-triyl, phenanthrene-1,3,8-triyl, phenanthrene-1,3,9-triyl, phenanthrene-1,6,7-triyl, phenanthrene-1,6,9-triyl, phenanthrene-1,7,9-triyl, phenanthrene-1,8,9-triyl, phenanthrene-1,9,10-triyl, phenanthrene-2,3,6-triyl, phenanthrene-2,3,7-triyl, phenanthrene-2,3,9-triyl, phenanthrene-2,7,9-triyl, phenanthrene-2,9,10-triyl, phenanthrene-3,6,7-triyl, phenanthrene-3,6,9-triyl, phenanthrene-3,9,10-triyl, anthracene-1,2,5-triyl, anthracene-1,2,6-triyl, anthracene-1,2,7-triyl, anthracene-1,2,8-triyl, anthracene-1,2,9-triyl, anthracene-1,2,10-triyl, anthracene-1,3,5-triyl, anthracene-1,3,6-triyl, anthracene-1,3,7-triyl, anthracene-1,3,8-triyl, anthracene-1,3,9-triyl, anthracene-1,3,10-triyl, anthracene-1,4,5-triyl, anthracene-1,4,6-triyl, anthracene-1,4,8-triyl, anthracene-1,4,9-triyl, anthracene-1,5,9-triyl, anthracene-1,6,7-triyl, anthracene-1,6,9-triyl, anthracene-1,7,9-triyl, anthracene-1,8,9-triyl, anthracene-1,9,10-triyl, anthracene-2,3,6-triyl, anthracene-2,3,9-triyl, anthracene-2,6,9-triyl, anthracene-2,7,9-triyl, anthracene-2,7,10-triyl, and anthracene-2,9,10-triyl group;

$A^4$ denotes a phenylene group;

a —$CH_2$— group included in $A^3$ and $A^4$ may be substituted with an —O— or a —S— group unless neighboring each other;

a —CH═ group included in $A^3$ and $A^4$ may be substituted with a —N═ group unless neighboring each other;

a hydrogen atom included in $A^3$ and $A^4$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;

$Z^4$ and $Z^5$ may be same or different, and denote —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —NHCO—, —N(CH$_3$)CO—, —N(C$_2$H$_5$)CO—, —N(C$_3$H$_7$)CO—, —N(C$_4$H$_9$)CO—, —CONH—, —CON(CH$_3$)—, —CON(C$_2$H$_5$)—, —CON(C$_3$H$_7$)—, —CON(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, —OCO—CH═CH— group, or a direct bond;

$L^3$ denotes an alkyl, alkenyl, or aralkyl with 12 carbon atoms or more, or a monovalent monocyclic or polycyclic hydrocarbon group with 12 carbon atoms or more, or a biphenyl group; the alkyl and alkenyl groups may be straight or branched; one or more hydrogen atoms included in the aralkyl and the monovalent monocyclic or polycyclic hydrocarbon groups may be substituted with a straight or branched alkyl or alkenyl group with 1 to 8 carbon atoms;

a —CH$_2$— group included in the alkyl, the alkenyl, and the monovalent monocyclic or polycyclic hydrocarbon group for $L^3$ may be substituted with —O—, —CO—, —COO—, —OCO—, —O—COO—, —OCH$_2$—, —CH$_2$O—, —C≡C—, —CH═CH—COO—, or —OCO—CH═CH— group unless oxygen atoms neighbor each other; and $n^3$ denotes 0 or 1;

the second monomer having a structure for producing a radical by light irradiation is at least one of: a compound represented by the following formula (4) and having a structure for producing a radical by hydrogen abstraction reaction by light irradiation, and a compound represented by the following formula (5) and having a structure for producing a radical by self-cleavage reaction by light irradiation;

the formula (4) being:

(4)

in the formula, $A^5$ denotes an aromatic ring;

$A^6$ denotes an aromatic ring same as or different from $A^5$, or a straight or branched alkyl or alkenyl group with 1 to 12 carbon atoms;

at least one of $A^5$ and $A^6$ contains -Sp$^3$-P group;

an aromatic ring included in at least one of $A^5$ and $A^6$ is a benzene ring or a biphenyl ring;

a hydrogen atom included in $A^5$ and $A^6$ may be substituted with -Sp$^3$-P group, a halogen atom, —CN, —NO$_2$, —NCO, —NCS, —OCN, —SCN, —SF$_5$, or an alkyl, alkenyl or aralkyl group with 1 to 12 carbon atoms and the alkyl and alkenyl groups may be straight or branched;

two neighboring hydrogen atoms included in $A^5$ and $A^6$ may be substituted with a straight or branched alkylene or alkenylene group with 1 to 12 carbon atoms to form a ring structure;

a hydrogen atom included in the alkyl, the alkenyl, the alkylene, the alkenylene or the aralkyl group of $A^5$ and $A^6$ may be substituted with -Sp$^3$-P group;

a —CH$_2$— group included in the alkyl, the alkenyl, the alkylene, the alkenylene or the aralkyl group of $A^5$ and $A^6$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, or —OCO—CH═CH— group unless an oxygen atom, a sulfur atom, and a nitrogen atom neighbor one another;

P denotes a radical polymerizable group;

Sp$^3$ denotes a straight, branched or cyclic alkylene or alkyleneoxy group with 1 to 6 carbon atoms, or a direct bond;

$m^1$ denotes 1 or 2;

a dotted line part connecting $A^5$ and Y and a dotted line part connecting $A^6$ and Y represent that a bond through Y may exist between $A^5$ and $A^6$; and Y denotes —CH$_2$—, —CH$_2$CH$_2$—, —CH═CH—, —O—, —S—, —NH—, —N(CH$_3$)—, —N(C$_2$H$_5$)—, —N(C$_3$F$_{17}$)—, —N(C$_4$H$_9$)—, —OCH$_2$—, —CH$_2$O—, —SCH$_2$—, —CH$_2$S— group, or a direct bond;

the formula (5) being:

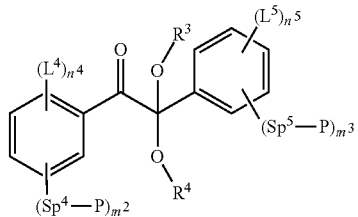

(5)

in the formula,

R$^3$ denotes a straight or branched alkyl or alkenyl group with 1 to 4 carbon atoms or -Sp$^6$-P;

R$^4$ denotes a straight or branched alkyl or alkenyl group with 1 to 4 carbon atoms or -Sp$^7$-P;

P denotes a same or different radical polymerizable group and a total number is 2 or more;

Sp$^4$ denotes a straight, branched, or cyclic alkylene, alkyleneoxy, or alkylenecarbonyloxy group with 1 to 6 carbon atoms, or a direct bond and may be same or different in the case where m$^2$ is 2 or more;

Sp$^5$ denotes a straight, branched, or cyclic alkylene, alkyleneoxy, or alkylenecarbonyloxy group with 1 to 6 carbon atoms, or a direct bond and may be same or different in the case where m$^3$ is 2 or more;

Sp$^6$ denotes a straight, branched, or cyclic alkylene, alkyleneoxy, or alkylenecarbonyloxy group with 1 to 6 carbon atoms;

Sp$^7$ denotes a straight, branched, or cyclic alkylene, alkyleneoxy, or alkylenecarbonyloxy group with 1 to 6 carbon atoms;

L$^4$ denotes —F, —OH, or a straight or branched alkyl, straight or branched alkenyl, or aralkyl group with 1 to 12 carbon atoms and may be same or different in the case where n$^4$ is 2 or more;

in the case where two L$^4$s are bonded to two neighboring carbon atoms in an aromatic ring, a ring structure may be formed by bonding each other and two L$^4$s may be same or different and be a straight or branched alkylene or alkenylene group with 1 to 12 carbon atoms;

L$^5$ denotes —F, —OH, or a straight or branched alkyl, straight or branched alkenyl, or aralkyl group with 1 to 12 carbon atoms and may be same or different in the case where n$^5$ is 2 or more;

in the case where two L$^5$s are bonded to two neighboring carbon atoms in an aromatic ring, a ring structure may be formed by bonding each other and the two L$^5$s may be same or different and be a straight or branched alkylene or alkenylene group with 1 to 12 carbon atoms;

one or more hydrogen atoms included in the alkyl, the alkenyl, the alkylene, the alkenylene or the aralkyl group of L$^4$ and L$^5$ may be substituted with —F or —OH group;

a —CH$_2$— group included in the alkyl, the alkenyl, the alkylene, the alkenylene or the aralkyl group of L$^4$ and L$^5$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, —OCO—CH═CH—, -Sp$^4$-P, or -Sp$^5$-P group unless an oxygen atom, a sulfur atom, and a nitrogen atom neighbor one another;

m$^2$ denotes an integer of 1 to 3;

m$^3$ denotes an integer of 0 to 3;

n$^4$ denotes an integer of 0 to 4;

n$^5$ denotes an integer of 0 to 4;

a total of m$^2$ and n$^4$ is an integer of 1 to 5;

a total of m$^3$ and n$^5$ is an integer of 0 to 5; and a total of m$^2$ and m$^3$ is an integer of 1 to 6.

2. The liquid crystal composition according to claim 1, wherein the first monomer produced by further bonding a hydrocarbon group with 12 carbon atoms or more to a compound produced by bonding two polymerizable groups to a cyclic aliphatic compound or aromatic compound with 6 carbon atoms or more is a compound represented by one of the following formulas (3-1) to (3-5):

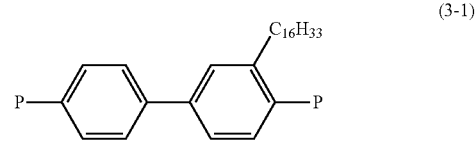

(3-1)

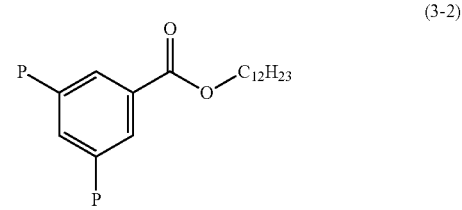

(3-2)

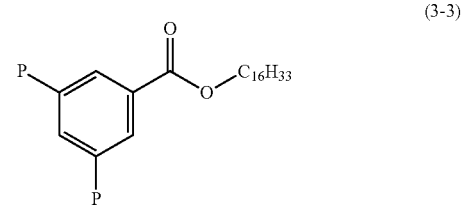

(3-3)

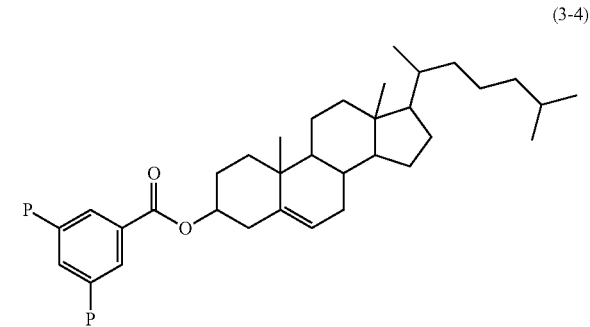

(3-4)

(3-5)

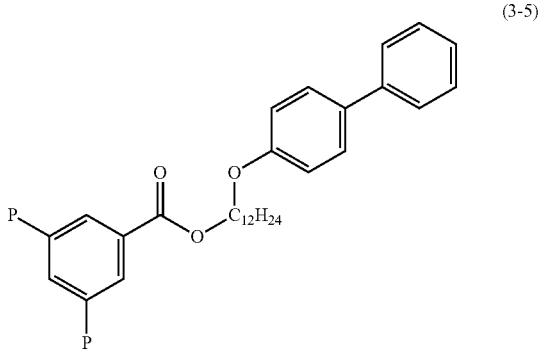

in the formula,
P and P are the same or different, and denote a radical polymerizable group.

3. A liquid crystal display device comprising:
a pair of substrates;
a liquid crystal layer sandwiched between the pair of the substrates and containing a liquid crystal material; and
a polymer layer formed on at least one of the pair of the substrates and configured to control alignment of liquid crystal molecules, wherein
the polymer layer is formed by polymerizing one or more kinds of monomers, and
the one or more monomers includes:
a first monomer produced by further bonding a hydrocarbon group with 12 carbon atoms or more to a compound produced by bonding two polymerizable groups to a cyclic aliphatic compound or aromatic compound with 6 carbon atoms or more; and
a second monomer having a structure for producing a radical by light irradiation; wherein
the first monomer produced by further bonding a hydrocarbon group with 12 carbon atoms or more to a compound produced by bonding two polymerizable groups to the cyclic aliphatic compound or aromatic compound with 6 carbon atoms or more is a compound represented by the following formula (2):

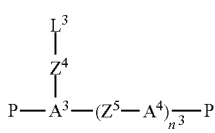
(2)

in the formula,
P and P are the same or different, and denote a (meth)acryloyloxy, (meth)acryloylamino, vinyl, or vinyloxy group;
$A^3$ denotes a trivalent, alicyclic, aromatic monocyclic, or condensed polycyclic hydrocarbon group;
the trivalent, alicyclic, aromatic monocyclic, or condensed polycyclic hydrocarbon group is selected from the group consisting of benzene-1,2,3-triyl, benzene-1,2,4-triyl, benzene-1,3,5-triyl, pyridine-2,3,4-triyl, pyridine-2,3,5-triyl, pyridine-2,4,6-triyl, naphthalene-1,2,5-triyl, naphthalene-1,2,6-triyl, naphthalene-1,2,7-triyl, naphthalene-1,2,8-triyl, naphthalene-1,3,5-triyl, naphthalene-1,3,6-triyl, naphthalene-1,3,7-triyl, naphthalene-1,3,8-triyl, naphthalene-1,4,5-triyl, naphthalene-1,4,6-triyl, naphthalene-1,4,7-triyl, naphthalene-1,6,7-triyl, naphthalene-1,6,8-triyl, naphthalene-2,3,6-triyl, cyclohexane-1,2,3-triyl, cyclohexane-1,2,4-triyl, cyclohexane-1,3,5-triyl, decahydronaphthalene-1,2,5-triyl, decahydronaphthalene-1,2,6-triyl, decahydronaphthalene-1,2,7-triyl, decahydronaphthalene-1,2,8-triyl, decahydronaphthalene-1,3,5-triyl, decahydronaphthalene-1,3,6-triyl, decahydronaphthalene-1,3,7-triyl, decahydronaphthalene-1,3,8-triyl, decahydronaphthalene-1,4,5-triyl, decahydronaphthalene-1,4,6-triyl, decahydronaphthalene-1,4,7-triyl, decahydronaphthalene-1,6,7-triyl, decahydronaphthalene-1,6,8-triyl, decahydronaphthalene-2,3,6-triyl, indan-1,1,5-triyl, indan-1,1,6-triyl, indan-1,3,5-triyl, indan-1,3,6-triyl, phenanthrene-1,2,6-triyl, phenanthrene-1,2,7-triyl, phenanthrene-1,2,8-triyl, phenanthrene-1,2,9-triyl, phenanthrene-1,3,6-triyl, phenanthrene-1,3,7-triyl, phenanthrene-1,3,8-triyl, phenanthrene-1,3,9-triyl, phenanthrene-1,6,7-triyl, phenanthrene-1,6,9-triyl, phenanthrene-1,7,9-triyl, phenanthrene-1,8,9-triyl, phenanthrene-1,9,10-triyl, phenanthrene-2,3,6-triyl, phenanthrene-2,3,7-triyl, phenanthrene-2,3,9-triyl, phenanthrene-2,7,9-triyl, phenanthrene-2,9,10-triyl, phenanthrene-3,6,7-triyl, phenanthrene-3,6,9-triyl, phenanthrene-3,9,10-triyl, anthracene-1,2,5-triyl, anthracene-1,2,6-triyl, anthracene-1,2,7-triyl, anthracene-1,2,8-triyl, anthracene-1,2,9-triyl, anthracene-1,2,10-triyl, anthracene-1,3,5-triyl, anthracene-1,3,6-triyl, anthracene-1,3,7-triyl, anthracene-1,3,8-triyl, anthracene-1,3,9-triyl, anthracene-1,3,10-triyl, anthracene-1,4,5-triyl, anthracene-1,4,6-triyl, anthracene-1,4,8-triyl, anthracene-1,4,9-triyl, anthracene-1,5,9-triyl, anthracene-1,6,7-triyl, anthracene-1,6,9-triyl, anthracene-1,7,9-triyl, anthracene-1,8,9-triyl, anthracene-1,9,10-triyl, anthracene-2,3,6-triyl, anthracene-2,3,9-triyl, anthracene-2,6,9-triyl, anthracene-2,7,9-triyl, anthracene-2,7,10-triyl, and anthracene-2,9,10-triyl group;
$A^4$ denotes a phenylene group;
a —$CH_2$— group included in $A^3$ and $A^4$ may be substituted with an —O— or a —S— group unless neighboring each other;
a —CH= group included in $A^3$ and $A^4$ may be substituted with a —N= group unless neighboring each other;
a hydrogen atom included in $A^3$ and $A^4$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;
$Z^4$ and $Z^5$ may be same or different, and denote —O—, —S—, —NH—, —CO—, —COO—, —OCO—, —O—COO—, —$OCH_2$—, —$CH_2O$—, —$SCH_2$—, —$CH_2S$—, —$N(CH_3)$—, —$N(C_2H_5)$—, —$N(C_3H_7)$—, —$N(C_4H_9)$—, —NHCO—, —$N(CH_3)$CO—, —$N(C_2H_5)$CO—, —$N(C_3H_7)$CO—, —$N(C_4H_9)$CO—, —CONH—, —$CON(CH_3)$—, —$CON(C_2H_5)$—, —$CON(C_3H_7)$—, —$CON(C_4H_9)$—, —$CF_2O$—, —$OCF_2$—, —$CF_2S$—, —$SCF_2$—, —$N(CF_3)$—, —$CH_2CH_2$—, —$CF_2CH_2$—, —$CH_2CF_2$—, —$CF_2CF_2$—, —CH=CH—, —CF=CF—, —C≡C—, —CH=CH—COO—, —OCO—CH=CH— group, or a direct bond;
$L^3$ denotes an alkyl, alkenyl, or aralkyl with 12 carbon atoms or more, or a monovalent monocyclic or polycyclic hydrocarbon group with 12 carbon atoms or more, or a biphenyl group; the alkyl and alkenyl groups may be straight or branched; one or more hydrogen atoms included in the aralkyl and the monovalent monocyclic or polycyclic hydrocarbon groups may be substituted with a straight or branched alkyl or alkenyl group with 1 to 8 carbon atoms;

a —$CH_2$— group included in the alkyl, the alkenyl, and the monovalent monocyclic or polycyclic hydrocarbon group for $L^3$ may be substituted with —O—, —CO—, —COO—, —OCO—, —O—COO—, —$OCH_2$—, —$CH_2O$—, —C≡C—, —CH=CH—COO—, or —OCO—CH=CH— group unless oxygen atoms neighbor each other; and $n^3$ denotes 0 or 1;

the second monomer having a structure for producing a radical by light irradiation is at least one of: a compound represented by the following formula (4) and having a structure for producing a radical by hydrogen abstraction reaction by light irradiation, and a compound represented by the following formula (5) and having a structure for producing a radical by self-cleavage reaction by light irradiation;

the formula (4) being:

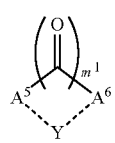

(4)

in the formula, $A^5$ denotes an aromatic ring;

$A^6$ denotes an aromatic ring same as or different from $A^5$, or a straight or branched alkyl or alkenyl group with 1 to 12 carbon atoms;

at least one of $A^5$ and $A^6$ contains -$Sp^3$-P group;

an aromatic ring included in at least one of $A^5$ and $A^6$ is a benzene ring or a biphenyl ring;

a hydrogen atom included in $A^5$ and $A^6$ may be substituted with -$Sp^3$-P group, a halogen atom, —CN, —$NO_2$, —NCO, —NCS, —OCN, —SCN, —$SF_5$, or an alkyl, alkenyl or aralkyl group with 1 to 12 carbon atoms and the alkyl and alkenyl groups may be straight or branched;

two neighboring hydrogen atoms included in $A^5$ and $A^6$ may be substituted with a straight or branched alkylene or alkenylene group with 1 to 12 carbon atoms to form a ring structure;

a hydrogen atom included in the alkyl, the alkenyl, the alkylene, the alkenylene or the aralkyl group of $A^5$ and $A^6$ may be substituted with -$Sp^3$-P group;

a —$CH_2$— group included in the alkyl, the alkenyl, the alkylene, the alkenylene or the aralkyl group of $A^5$ and $A^6$ may be substituted with —O—, —S—, —NH—, —CO—, —COO—, —OCO—, —O—COO—, —$OCH_2$—, —$CH_2O$—, —$SCH_2$—, —$CH_2S$—, —$N(CH_3)$—, —$N(C_2H_5)$—, —$N(C_3H_7)$—, —$N(C_4H_9)$—, —$CF_2O$—, —$OCF_2$—, —$CF_2S$—, —$SCF_2$—, —$N(CF_3)$—, —$CH_2CH_2$—, —$CF_2CH_2$—, —$CH_2CF_2$—, —$CF_2CF_2$—, —CH=CH—, —CF=CF—, —C≡C—, —CH=CH—COO—, or —OCO—CH=CH— group unless an oxygen atom, a sulfur atom, and a nitrogen atom neighbor one another;

P denotes a radical polymerizable group;

$Sp^3$ denotes a straight, branched or cyclic alkylene or alkyleneoxy group with 1 to 6 carbon atoms, or a direct bond;

$m^1$ denotes 1 or 2;

a dotted line part connecting $A^5$ and Y and a dotted line part connecting $A^6$ and Y represent that a bond through Y may exist between $A^5$ and $A^6$; and Y denotes —$CH_2$—, —$CH_2CH_2$—, —CH=CH—, —O—, —S—, —NH—, —$N(CH_3)$—, —$N(C_2H_5)$—, —$N(C_3F_{17})$—, —$N(C_4H_9)$—, —$OCH_2$—, —$CH_2O$—, —$SCH_2$—, —$CH_2S$— group, or a direct bond;

the formula (5) being:

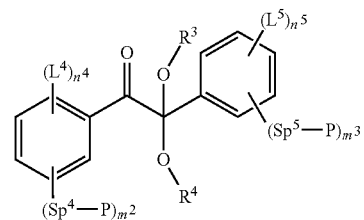

(5)

in the formula, $R^3$ denotes a straight or branched alkyl or alkenyl group with 1 to 4 carbon atoms or -$Sp^6$-P;

$R^4$ denotes a straight or branched alkyl or alkenyl group with 1 to 4 carbon atoms or -$Sp^7$-P;

P denotes a same or different radical polymerizable group and a total number is 2 or more;

$Sp^4$ denotes a straight, branched, or cyclic alkylene, alkyleneoxy, or alkylenecarbonyloxy group with 1 to 6 carbon atoms, or a direct bond and may be same or different in the case where $m^2$ is 2 or more;

$Sp^5$ denotes a straight, branched, or cyclic alkylene, alkyleneoxy, or alkylenecarbonyloxy group with 1 to 6 carbon atoms, or a direct bond and may be same or different in the case where $m^3$ is 2 or more;

$Sp^6$ denotes a straight, branched, or cyclic alkylene, alkyleneoxy, or alkylenecarbonyloxy group with 1 to 6 carbon atoms;

$Sp^7$ denotes a straight, branched, or cyclic alkylene, alkyleneoxy, or alkylenecarbonyloxy group with 1 to 6 carbon atoms;

$L^4$ denotes —F, —OH, or a straight or branched alkyl, straight or branched alkenyl, or aralkyl group with 1 to 12 carbon atoms and may be same or different in the case where $n^4$ is 2 or more;

in the case where two $L^4$s are bonded to two neighboring carbon atoms in an aromatic ring, a ring structure may be formed by bonding each other and two $L^4$s may be same or different and be a straight or branched alkylene or alkenylene group with 1 to 12 carbon atoms;

$L^5$ denotes —F, —OH, or a straight or branched alkyl, straight or branched alkenyl, or aralkyl group with 1 to 12 carbon atoms and may be same or different in the case where $n^5$ is 2 or more;

in the case where two $L^5$s are bonded to two neighboring carbon atoms in an aromatic ring, a ring structure may be formed by bonding each other and the two $L^5$s may be same or different and be a straight or branched alkylene or alkenylene group with 1 to 12 carbon atoms;

one or more hydrogen atoms included in the alkyl, the alkenyl, the alkylene, the alkenylene or the aralkyl group of $L^4$ and $L^5$ may be substituted with —F or —OH group;

a —CH$_2$— group included in the alkyl, the alkenyl, the alkylene, the alkenylene or the aralkyl group of $L^4$ and $L^5$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, —OCO—CH=CH—, -Sp$^4$-P, or -Sp$^5$-P group unless an oxygen atom, a sulfur atom, and a nitrogen atom neighbor one another;

$m^2$ denotes an integer of 1 to 3;
$m^3$ denotes an integer of 0 to 3;
$n^4$ denotes an integer of 0 to 4;
$n^5$ denotes an integer of 0 to 4;
a total of $m^2$ and $n^4$ is an integer of 1 to 5;
a total of $m^3$ and $n^5$ is an integer of 0 to 5; and
a total of $m^2$ and $m^3$ is an integer of 1 to 6.

4. The liquid crystal display device according to claim 3, wherein the first monomer produced by further bonding a hydrocarbon group with 12 carbon atoms or more to a compound produced by bonding two polymerizable groups to a cyclic aliphatic compound or aromatic compound with 6 carbon atoms or more is a compound represented by one of the following formulas (3-1) to (3-5):

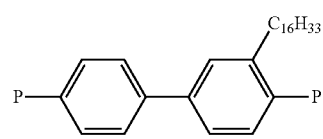
(3-1)

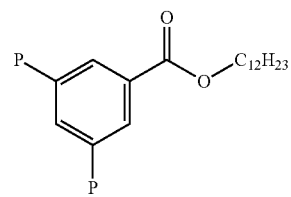
(3-2)

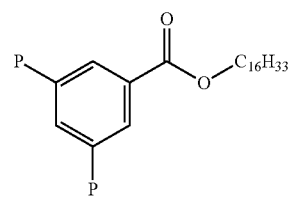
(3-3)

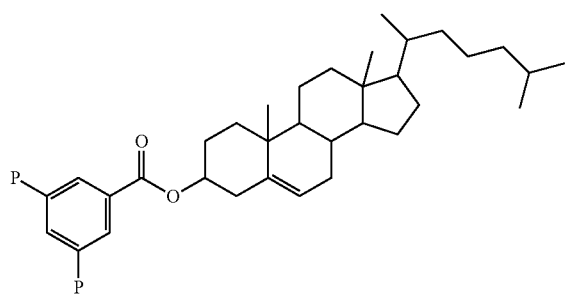
(3-4)

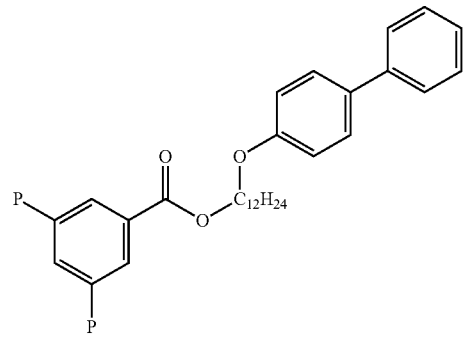
(3-5)

in the formula, P and P are the same or different, and denote a radical polymerizable group.

5. A production method for a liquid crystal display device comprising:
injecting a liquid crystal composition containing a liquid crystal material and one or more kinds of monomers between a pair of substrates; and
forming a polymer layer for controlling alignment of liquid crystal molecules on a substrate by polymerizing the monomers by radiating the liquid crystal composition with light,
the one or more monomers including:
a first monomer produced by further bonding a hydrocarbon group with 12 carbon atoms or more to a compound produced by bonding two polymerizable groups to a cyclic aliphatic compound or aromatic compound with 6 carbon atoms or more; and
a second monomer having a structure for producing a radical by light irradiation, wherein
the first monomer produced by further bonding a hydrocarbon group with 12 carbon atoms or more to a compound produced by bonding two polymerizable groups to the cyclic aliphatic compound or aromatic compound with 6 carbon atoms or more is a compound represented by the following formula (2):

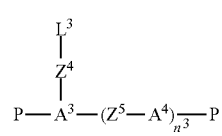
(2)

in the formula,
P and P are the same or different, and denote a (meth)acryloyloxy, (meth)acryloylamino, vinyl, or vinyloxy group;
$A^3$ denotes a trivalent, alicyclic, aromatic monocyclic, or condensed polycyclic hydrocarbon group;
the trivalent, alicyclic, aromatic monocyclic, or condensed polycyclic hydrocarbon group is selected from the group consisting of benzene-1,2,3-triyl, benzene-1,2,4-triyl, benzene-1,3,5-triyl, pyridine-2,3,4-triyl, pyridine-2,3,5-triyl, pyridine-2,4,6-triyl, naphthalene-1,2,5-triyl, naphthalene-1,2,6-triyl, naphthalene-1,2,7-triyl, naphthalene-1,2,8-triyl, naphthalene-1,3,5-triyl, naphthalene-1,3,6-triyl, naphthalene-1,3,7-triyl, naphthalene-1,3,8-triyl, naphthalene-1,4,5-triyl, naphthalene-1,4,6-triyl, naphthalene-1,4,7-triyl, naphthalene-1,6,7-triyl, naphthalene-1,6,8-triyl, naphthalene-2,3,6-triyl, cyclohexane-1,2,3-triyl, cyclohexane-1,2,4-triyl, cyclohexane-1,3,5-triyl, decahydronaphthalene-1,2,5-triyl, decahydronaphthalene-1,2,6-triyl, decahydronaphthalene-1,2,7-triyl, decahydronaphthalene-1,2,8-triyl, decahydronaphthalene-1,3,5-triyl, decahydronaphthalene-1,3,6-triyl, decahydronaphthalene-1,3,7-triyl, decahydronaphthalene-1,3,8-triyl, decahydronaphthalene-1,4,5-triyl, decahydronaphthalene-1,4,6-triyl, decahydronaphthalene-1,4,7-triyl, decahydronaphthalene-1,6,7-triyl, decahydronaphthalene-1,6,8-triyl, decahydronaphthalene-2,3,6-triyl, indan-1,1,5-triyl, indan-1,1,6-triyl, indan-1,3,5-triyl, indan-1,3,6-triyl, phenanthrene-1,2,6-triyl, phenanthrene-1,2,7-triyl, phenanthrene-1,2,8-triyl, phenanthrene-1,2,9-triyl, phenanthrene-1,3,6-triyl, phenanthrene-1,3,7-triyl, phenanthrene-1,3,8-triyl, phenanthrene-1,3,9-triyl, phenanthrene-1,6,7-triyl, phenanthrene-1,6,9-triyl, phenanthrene-1,7,9-triyl, phenanthrene-1,8,9-triyl, phenanthrene-1,9,10-triyl, phenanthrene-2,3,6-triyl, phenanthrene-2,3,7-triyl, phenanthrene-2,3,9-triyl, phenanthrene-2,7,9-triyl, phenanthrene-2,9,10-triyl, phenanthrene-3,6,7-triyl, phenanthrene-3,6,9-triyl, phenanthrene-3,9,10-triyl, anthracene-1,2,5-triyl, anthracene-1,2,6-triyl, anthracene-1,2,7-triyl, anthracene-1,2,8-triyl, anthracene-1,2,9-triyl, anthracene-1,2,10-triyl, anthracene-1,3,5-triyl, anthracene-1,3,6-triyl, anthracene-1,3,7-triyl, anthracene-1,3,8-triyl, anthracene-1,3,9-triyl, anthracene-1,3,10-triyl, anthracene-1,4,5-triyl, anthracene-1,4,6-triyl, anthracene-1,4,8-triyl, anthracene-1,4,9-triyl, anthracene-1,5,9-triyl, anthracene-1,6,7-triyl, anthracene-1,6,9-triyl, anthracene-1,7,9-triyl, anthracene-1,8,9-triyl, anthracene-1,9,10-triyl, anthracene-2,3,6-triyl, anthracene-2,3,9-triyl, anthracene-2,6,9-triyl, anthracene-2,7,9-triyl, anthracene-2,7,10-triyl, and anthracene-2,9,10-triyl group;

$A^4$ denotes a phenylene group;

a —$CH_2$— group included in $A^3$ and $A^4$ may be substituted with an —O— or a —S— group unless neighboring each other;

a —CH= group included in $A^3$ and $A^4$ may be substituted with a —N= group unless neighboring each other;

a hydrogen atom included in $A^3$ and $A^4$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;

$Z^4$ and $Z^5$ may be same or different, and denote —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —NHCO—, —N(CH$_3$)CO—, —N(C$_2$H$_5$)CO—, —N(C$_3$H$_7$)CO—, —N(C$_4$H$_9$)CO—, —CONH—, —CON(CH$_3$)—, —CON(C$_2$H$_5$)—, —CON(C$_3$H$_7$)—, —CON(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, —OCO—CH=CH— group, or a direct bond;

$L^3$ denotes an alkyl, alkenyl, or aralkyl with 12 carbon atoms or more, or a monovalent monocyclic or polycyclic hydrocarbon group with 12 carbon atoms or more, or a biphenyl group; the alkyl and alkenyl groups may be straight or branched; one or more hydrogen atoms included in the aralkyl and the monovalent monocyclic or polycyclic hydrocarbon groups may be substituted with a straight or branched alkyl or alkenyl group with 1 to 8 carbon atoms;

a —$CH_2$— group included in the alkyl, the alkenyl, and the monovalent monocyclic or polycyclic hydrocarbon group for $L^3$ may be substituted with —O—, —CO—, —COO—, —OCO—, —O—COO—, —OCH$_2$—, —CH$_2$O—, —C≡C—, —CH=CH—COO—, or —OCO—CH=CH— group unless oxygen atoms neighbor each other; and $n^3$ denotes 0 or 1;

the second monomer having a structure for producing a radical by light irradiation is at least one of: a compound represented by the following formula (4) and having a structure for producing a radical by hydrogen abstraction reaction by light irradiation, and a compound represented by the following formula (5) and having a structure for producing a radical by self-cleavage reaction by light irradiation, the formula (4) being:

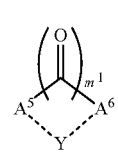

(4)

in the formula, $A^5$ denotes an aromatic ring;

$A^6$ denotes an aromatic ring same as or different from $A^5$, or a straight or branched alkyl or alkenyl group with 1 to 12 carbon atoms;

at least one of $A^5$ and $A^6$ contains -Sp$^3$-P group;

an aromatic ring included in at least one of $A^5$ and $A^6$ is a benzene ring or a biphenyl ring;

a hydrogen atom included in $A^5$ and $A^6$ may be substituted with -Sp$^3$-P group, a halogen atom, —CN, —NO$_2$, —NCO, —NCS, —OCN, —SCN, —SF$_5$, or an alkyl, alkenyl or aralkyl group with 1 to 12 carbon atoms and the alkyl and alkenyl groups may be straight or branched;

two neighboring hydrogen atoms included in $A^5$ and $A^6$ may be substituted with a straight or branched alkylene or alkenylene group with 1 to 12 carbon atoms to form a ring structure;

a hydrogen atom included in the alkyl, the alkenyl, the alkylene, the alkenylene or the aralkyl group of $A^5$ and $A^6$ may be substituted with -Sp$^3$-P group;

a —$CH_2$— group included in the alkyl, the alkenyl, the alkylene, the alkenylene or the aralkyl group of $A^5$ and $A^6$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, or —OCO—CH=CH— group unless an oxygen atom, a sulfur atom, and a nitrogen atom neighbor one another;

P denotes a radical polymerizable group;

Sp$^3$ denotes a straight, branched or cyclic alkylene or alkyleneoxy group with 1 to 6 carbon atoms, or a direct bond;

$m^1$ denotes 1 or 2;

a dotted line part connecting $A^5$ and Y and a dotted line part connecting $A^6$ and Y represent that a bond through Y may exist between $A^5$ and $A^6$; and Y denotes —$CH_2$—, —$CH_2CH_2$—, —CH=CH—, —O—, —S—, —NH—, —N($CH_3$)—, —N($C_2H_5$)—, —N($C_3H_7$)—, —N($C_4H_9$)—, —$OCH_2$—, —$CH_2O$—, —$SCH_2$—, —$CH_2S$— group, or a direct bond;

the formula (5) being:

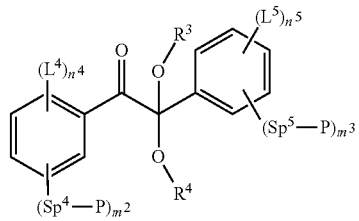

(5)

in the formula, $R^3$ denotes a straight or branched alkyl or alkenyl group with 1 to 4 carbon atoms or -$Sp^6$-P;

$R^4$ denotes a straight or branched alkyl or alkenyl group with 1 to 4 carbon atoms or -$Sp^7$-P;

P denotes a same or different radical polymerizable group and a total number is 2 or more;

$Sp^4$ denotes a straight, branched, or cyclic alkylene, alkyleneoxy, or alkylenecarbonyloxy group with 1 to 6 carbon atoms, or a direct bond and may be same or different in the case where $m^2$ is 2 or more;

$Sp^5$ denotes a straight, branched, or cyclic alkylene, alkyleneoxy, or alkylenecarbonyloxy group with 1 to 6 carbon atoms, or a direct bond and may be same or different in the case where $m^3$ is 2 or more;

$Sp^6$ denotes a straight, branched, or cyclic alkylene, alkyleneoxy, or alkylenecarbonyloxy group with 1 to 6 carbon atoms;

$Sp^7$ denotes a straight, branched, or cyclic alkylene, alkyleneoxy, or alkylenecarbonyloxy group with 1 to 6 carbon atoms;

$L^4$ denotes —F, —OH, or a straight or branched alkyl, straight or branched alkenyl, or aralkyl group with 1 to 12 carbon atoms and may be same or different in the case where $n^4$ is 2 or more;

in the case where two $L^4$s are bonded to two neighboring carbon atoms in an aromatic ring, a ring structure may be formed by bonding each other and two $L^4$s may be same or different and be a straight or branched alkylene or alkenylene group with 1 to 12 carbon atoms;

$L^5$ denotes —F, —OH, or a straight or branched alkyl, straight or branched alkenyl, or aralkyl group with 1 to 12 carbon atoms and may be same or different in the case where $n^5$ is 2 or more;

in the case where two $L^5$s are bonded to two neighboring carbon atoms in an aromatic ring, a ring structure may be formed by bonding each other and the two $L^5$s may be same or different and be a straight or branched alkylene or alkenylene group with 1 to 12 carbon atoms;

one or more hydrogen atoms included in the alkyl, the alkenyl, the alkylene, the alkenylene or the aralkyl group of $L^4$ and $L^5$ may be substituted with —F or —OH group;

a —$CH_2$— group included in the alkyl, the alkenyl, the alkylene, the alkenylene or the aralkyl group of $L^4$ and $L^5$ may be substituted with —O—, —S—, —NH—, —CO—, —COO—, —OCO—, —O—COO—, —$OCH_2$—, —$CH_2O$—, —$SCH_2$—, —$CH_2S$—, —N($CH_3$)—, —N($C_2H_5$)—, —N($C_3H_7$)—, —N($C_4H_9$)—, —$CF_2O$—, —$OCF_2$—, —$CF_2S$—, —$SCF_2$—, —N($CF_3$)—, —$CH_2CH_2$—, —$CF_2CH_2$—, —$CH_2CF_2$—, —$CF_2CF_2$—, —CH=CH—, —CF=CF—, —C≡C—, —CH=CH—COO—, —OCO—CH=CH—, -$Sp^4$-P, or -$Sp^5$-P group unless an oxygen atom, a sulfur atom, and a nitrogen atom neighbor one another;

$m^2$ denotes an integer of 1 to 3;

$m^3$ denotes an integer of 0 to 3;

$n^4$ denotes an integer of 0 to 4;

$n^5$ denotes an integer of 0 to 4;

a total of $m^2$ and $n^4$ is an integer of 1 to 5;

a total of $m^3$ and $n^5$ is an integer of 0 to 5; and a total of $m^2$ and $m^3$ is an integer of 1 to 6.

6. The liquid crystal composition according to claim 1, wherein $L^3$ in the formula (2) includes a cholesteryl group or a biphenyl group.

7. The liquid crystal display device according to claim 3, wherein $L^3$ in the formula (2) includes a cholesteryl group or a biphenyl group.

8. The production method for a liquid crystal display device according to claim 5, wherein $L^3$ in the formula (2) includes a cholesteryl group or a biphenyl group.

9. A liquid crystal composition comprising:

a liquid crystal material; and one or more kinds of monomers, at least one of the monomers being a compound produced by further bonding a hydrocarbon group with 12 carbon atoms or more to a compound produced by bonding two polymerizable groups to a cyclic aliphatic compound or aromatic compound with 6 carbon atoms or more, wherein the compound produced by further bonding a hydrocarbon group with 12 carbon atoms or more to a compound produced by bonding two polymerizable groups to a cyclic aliphatic compound or aromatic compound with 6 carbon atoms or more is a compound represented by one of the following formulas (3-1) to (3-5):

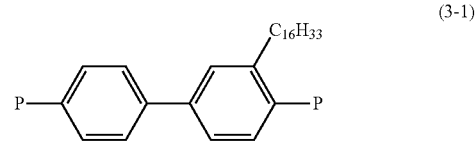

(3-1)

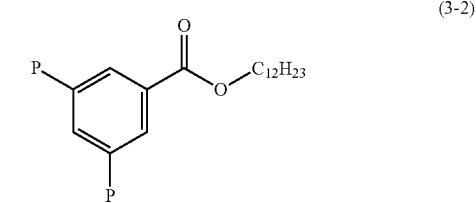

(3-2)

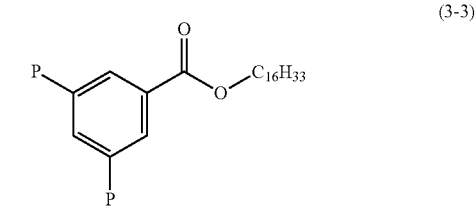

(3-3)

(3-4)

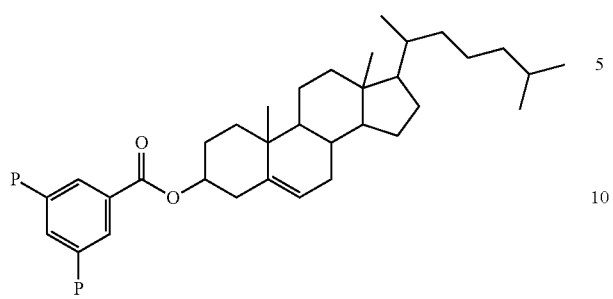

(3-5)

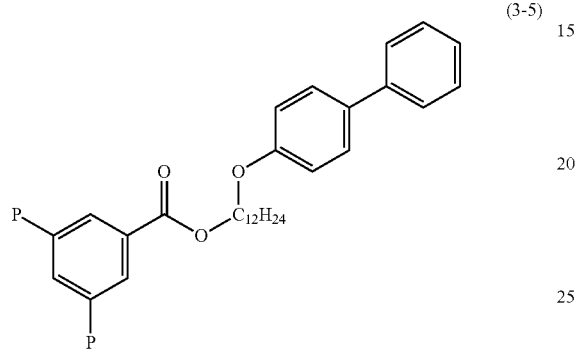

in the formula, P and P are the same or different, and denote a radical polymerizable group.

10. A liquid crystal display device comprising:
a pair of substrates;
a liquid crystal layer sandwiched between the pair of the substrates and containing a liquid crystal material; and
a polymer layer formed on at least one of the pair of the substrates and configured to control alignment of liquid crystal molecules, wherein
the polymer layer is formed by polymerizing one or more kind of monomers,
at least one of the monomers being a compound produced by further bonding a hydrocarbon group with 12 carbon atoms or more to a compound produced by bonding two polymerizable groups to a cyclic aliphatic compound or aromatic compound with 6 carbon atoms or more,
the compound produced by further bonding a hydrocarbon group with 12 carbon atoms or more to a compound produced by bonding two polymerizable groups to a cyclic aliphatic compound or aromatic compound with 6 carbon atoms or more is a compound represented by one of the following formulas (3-1) to (3-5):

(3-1)

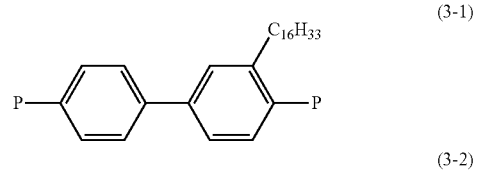

(3-2)

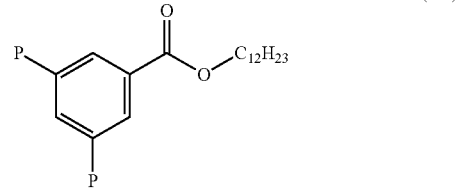

(3-3)

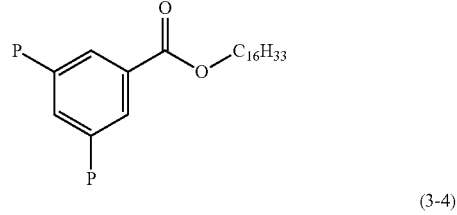

(3-4)

(3-5)

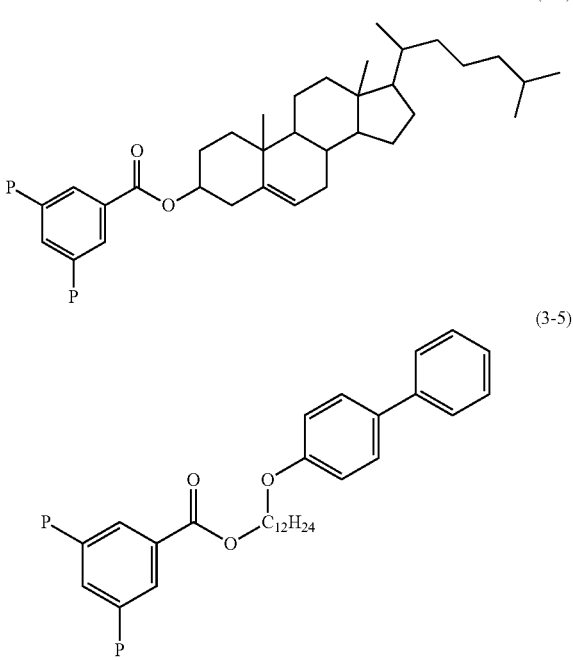

in the formula, P and P are the same or different, and denote a radical polymerizable group.

11. A production method for a liquid crystal display device comprising:
injecting a liquid crystal composition containing a liquid crystal material and one or more kind of monomers between a pair of substrates; and
forming a polymer layer for controlling alignment of liquid crystal molecules on a substrate by polymerizing the monomers by radiating the liquid crystal composition with light,
at least one of the monomers being a compound produced by further bonding a hydrocarbon group with 12 carbon atoms or more to a compound produced by bonding two polymerizable groups to a cyclic aliphatic compound or aromatic compound with 6 carbon atoms or more, wherein
the compound produced by further bonding a hydrocarbon group with 12 carbon atoms or more to a compound produced by bonding two polymerizable groups to a cyclic aliphatic compound or aromatic compound with 6 carbon atoms or more is a compound represented by one of the following formulas (3-1) to (3-5):

(3-1)

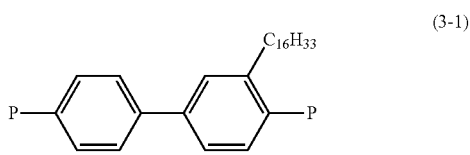

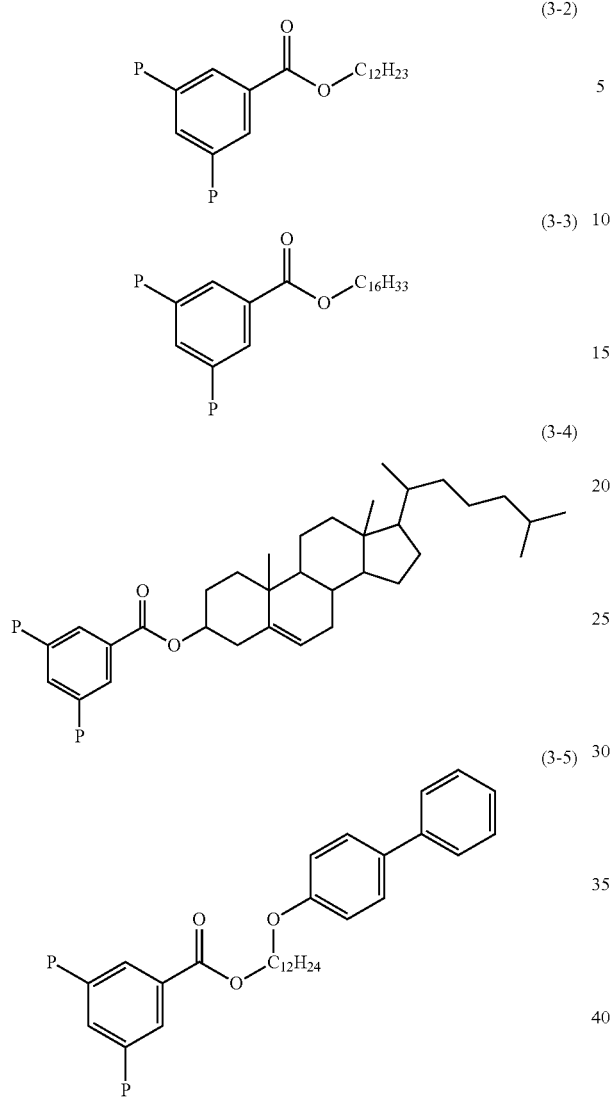

in the formula, P and P are the same or different, and denote a radical polymerizable group.

12. The liquid crystal composition according to claim 9, wherein P and P are the same or different, and denote a (meth)acryloyloxy, (meth)acryloylamino, vinyl, or vinyloxy group.

13. The liquid crystal display device according to claim 10, wherein P and P are the same or different, and denote a (meth)acryloyloxy, (meth)acryloylamino, vinyl, or vinyloxy group.

14. The production method for a liquid crystal display device according to claim 11, wherein P and P are the same or different, and denote a (meth)acryloyloxy, (meth)acryloylamino, vinyl, or vinyloxy group.

15. A monomer being a compound represented by the following formulas (3-1) to (3-5):

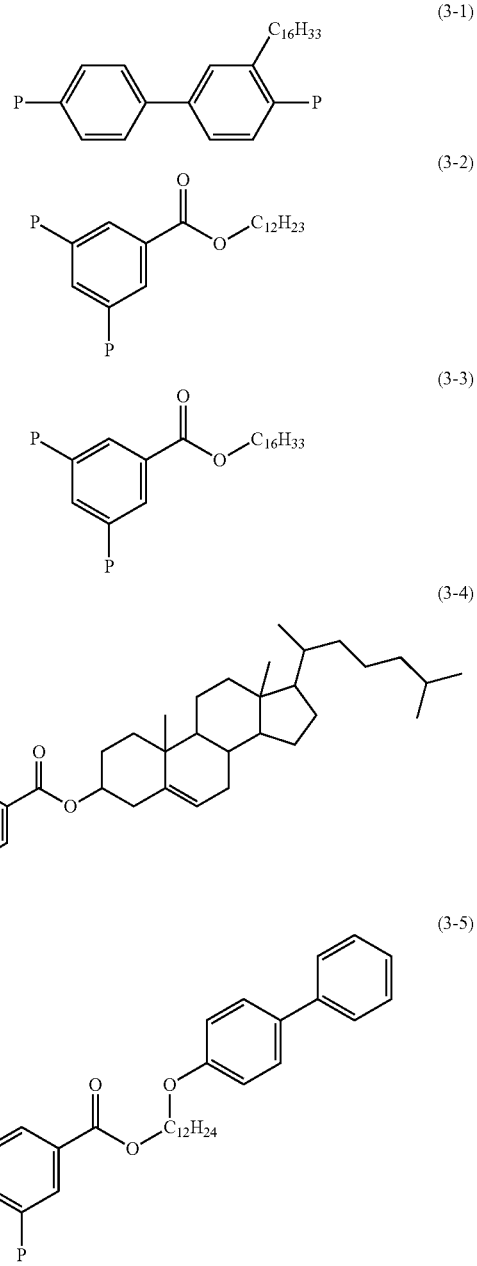

in the formula, P and P are the same or different, and denote a (meth)acryloyloxy, (meth)acryloylamino, vinyl, or vinyloxy group.

* * * * *